United States Patent
Ghosh et al.

(10) Patent No.: US 11,319,548 B2
(45) Date of Patent: May 3, 2022

(54) COLD- AND WATER-INDUCIBLE PROMOTER FROM RICE

(71) Applicant: Maharashtra Hybrid Seeds Company Private Limited (MAHYCO), Jalna (IN)

(72) Inventors: Paramita Ghosh, Pune (IN); Anjanabha Bhattacharya, Kolkata (IN); Anindya Bandopadhyay, Metro Manila (PH); Bharat Char, Dawalwadi (IN)

(73) Assignee: MAHARASHTRA HYBRID SEEDS COMPANY PRIVATE LIMITED (MAHYCO), Maharashtra (IN)

( * ) Notice: Subject to any disclaimer, the term of this patent is extended or adjusted under 35 U.S.C. 154(b) by 408 days.

(21) Appl. No.: 16/089,288

(22) PCT Filed: Apr. 1, 2017

(86) PCT No.: PCT/IN2017/050123
§ 371 (c)(1),
(2) Date: Sep. 27, 2018

(87) PCT Pub. No.: WO2017/168452
PCT Pub. Date: Oct. 5, 2017

(65) Prior Publication Data
US 2020/0299707 A1    Sep. 24, 2020

(30) Foreign Application Priority Data
Apr. 1, 2016  (IN) .............................. 201611011694

(51) Int. Cl.
*C12N 15/82*    (2006.01)
(52) U.S. Cl.
CPC ..... *C12N 15/8237* (2013.01); *C12N 15/8205* (2013.01)
(58) Field of Classification Search
None
See application file for complete search history.

(56) References Cited

U.S. PATENT DOCUMENTS

| | | |
|---|---|---|
| 2005/0155114 A1 | 7/2005 | Hinchey |
| 2007/0020621 A1 | 1/2007 | Boukharov |
| 2009/0229014 A1 | 9/2009 | Deng |

FOREIGN PATENT DOCUMENTS

CN    101831430 A    9/2010

OTHER PUBLICATIONS

Kim et al. A novel oxidative stress-inducible peroxidase promoter from sweetpotato: molecular cloning and characterization in transgenic tobacco plants and cultured cells. (2003) Plant Molecular Biology; vol. 51; pp. 831-838 (Year: 2003).*
Dezar et al. The promoter of the sunflower HD-Zip protein gene Hahb4 directs tissue-specific expression and is inducible by water stress, high salt concentrations and ABA. (2005) Plant Science; vol. 169; pp. 447-456 (Year: 2005).*
Duan et al. Identification of a regulatory element responsible for salt induction of rice OsRAV2 through ex situ and in situ promoter analysis. (2016) Plant. Mol. Biol.; vol. 90; pp. 49-62 (Year: 2016).*
McCombie et al. Genomic sequence or *Oryza sativa*, Nipponbare strain, clone OSJNBb0096L14, from chromosome 3, complete sequence. (2002) Gen Bank Accession AC129008; pp. 1-29 (Year: 2002).*
International Search Report in PCT/IN2017/050123, dated Jul. 26, 2017.
"Rice Drought Stress Induced Expression Promotor (PosDro2), SEQ ID 1." XP002771702, retrieved from EBI Accession No. GSN:BBK80896.
"Rice Genomic Promoter Sequence SEQ ID No. 4007." XP002771703, retrieved from EBI Accession No. GSN:A0B59072.
Database WPI Week 201073 Thomson Scientific, London GB AN 2010-N15556 XP002771704.
Joshee, et al. "Isolation and characterization of a water stress-specific genomic gene, pwsi 18, from rice." Plant and cell physiology 39, No. 1 (1998): 64-72.
Kim, et al. "Functional analysis of a cold-responsive rice WRKY gene, OsWRKY71." Plant Biotechnology Reports 10, No. 1 (2016): 13-23.
Rai, et al. "Comparative functional analysis of three abiotic stress-inducible promoters in transgenic rice." Transgenic research 18, No. 5 (2009): 787-799.

* cited by examiner

*Primary Examiner* — Cathy Kingdon Worley
(74) *Attorney, Agent, or Firm* — Kipatrick Townsend & Stockton LLP

(57) ABSTRACT

This present invention relates to isolation and derivation of nucleic acid sequences from monocot plants, preferably rice that are capable of driving and/or regulating a stress induced expression of an operably linked nucleic acid. The present invention also is directed to the use of the isolated nucleic acid to drive and/or regulate a stress-induced expression of an operably linked nucleic acid. The isolated nucleic acid sequence of the present invention as set forth in SEQ ID NO 3 or SEQ ID NO 6 or SEQ ID NO 7 or SEQ ID NO 9 or the complement thereof can be an inducible promoter. The promoters of the invention can be induced by abiotic stress such as water, cold, heat and/or salinity or a biotic stress such as by a virus, bacteria, or fungi.

13 Claims, 10 Drawing Sheets
Specification includes a Sequence Listing.

Fig. 3: RP8 promoter regulated GUS expression under water stress

Fig. 4: RP10 promoter regulated GUS expression under water stress

SEQUENCE LISTING

<160> NUMBER OF SEQ ID NOS: 30

<210> SEQ ID NO 1
<211> LENGTH: 1988
<212> TYPE: DNA
<213> ORGANISM: Oryza sativa

<400> SEQUENCE: 1

| | | | | | | |
|---|---|---|---|---|---|---|
| caccgcggcc | gctctctgtg | gctgttgtgt | cgttcccggc | gaagtcaacg | ggaaggtgaa | 60 |
| aagaaggaaa | gagaagggc | aatatgggca | tttaaaaaat | atctcacctc | ttttgacctg | 120 |
| gaaataataa | aataatacga | ccgatgtcct | atggctaatt | atactttttt | agtgtccatc | 180 |
| agccgtatta | tattttcgcg | gtgtctctca | gccaattaca | cgttttttta | cgtgtcctgt | 240 |
| ggtaaatttt | gtctattata | taacggggta | aaaccgatac | aataaattat | ctcaatttat | 300 |
| aatactctgc | tcatgcatcg | actcatccat | acgtgtttca | tacgtgtttc | tttatatccc | 360 |
| gtcaattttt | aagtaccacc | tacgtgtcag | agaccagaga | tctacctctt | ctgaacgtac | 420 |
| cacctactac | aatttttaag | attgtccttg | taagtcaaga | ttgaagtcct | ttcatgcccc | 480 |
| gccaaaaaaa | ttcctttcat | gaatgccatg | ttatactccc | tccatcctcg | tcttatttaa | 540 |
| aaaaattatg | caaatataaa | aataaaaagt | tgtgcttaaa | ataatttgaa | taataaagta | 600 |
| agtcaaaata | ataataataa | taatttcaaa | attttttaaa | taagacgatt | ggtcaaacag | 660 |
| tgcaaacaaa | aattcaaaat | cccttatatt | atgagacgga | gggagtaaaa | aacttgtggg | 720 |
| ttatgccagg | gccatgttat | aaaaactttt | tattattgat | tcacaatttg | tgttcgacga | 780 |
| taaccttttt | tcttggggaa | tagtaacatt | ttagtgtgta | tgagctgttg | gcgactaatt | 840 |
| tttacaggaa | atttaattt | catcactaat | aagtttggca | gttatccaaa | tgtcccttta | 900 |
| gatttgctct | cttttttacc | actctaaaga | gatggtttct | actttgccc | acgtggcatg | 960 |
| tgaatgtggc | aactgagcgt | gaacaatggt | gtgggaccca | gtagttagat | aggtgaagag | 1020 |
| aggaggggaa | ggggtccacg | tgggtcacac | gctgactcaa | ctgccacgtc | aggtaaaacc | 1080 |
| aaggataaaa | ccgtctaacg | acttagagtg | atctggtttt | gtaagttaag | agatgcatat | 1140 |
| atatatatat | atctgttttt | ttcggtttat | gaacgatttt | gtaactcggc | ggtaagatga | 1200 |
| gggacctccg | gtatacctt | tcccgtcaag | ttgaagctcg | gcccactgct | tgcttcttgg | 1260 |
| cggcccatat | gcagaactaa | tggtttggtc | gttgttcgtc | aaatcaaaac | tactccaggt | 1320 |
| ggcatggatt | tcgttgacaa | caagagaaaa | cgacaaggcg | caccagctag | ctggagacca | 1380 |
| ccaaatctaa | tcatgcagta | cgagcgccag | tggtcaacca | gagatgaaaa | gacacgagtc | 1440 |
| ctcagatcga | ttgccttctc | tcgaagcttc | cgtaatccaa | actgaagtgc | tctgcatgga | 1500 |
| ctcatctctg | catgcattcc | atcctacaga | tttacctaca | ttggctcaca | cgccccaaca | 1560 |
| tgatcgaata | cgtcacactc | gtgcgttcaa | tcgattggaa | gctagctagc | cgtgtttagt | 1620 |
| ggatcgaatg | atcgacgtac | gattgatcga | tcggtacgta | catgggttga | tcagctcggt | 1680 |
| ccggtctgcc | ttacgtacgt | gtcgctcgga | ttgctgagga | gagcgcgccc | aaatctgcgg | 1740 |
| gacaggccgg | attgctccac | tacgcgacgc | cctccgccgg | ccgcggccac | aacctcgcga | 1800 |
| caccgacgca | aatcccacta | aaaccttacg | acacgacgag | ccgcgctagc | taccgcacgc | 1860 |
| atgcgtacca | ccacaaccgc | gcgcgctccc | tataaatttc | accgctaaat | cccaccacga | 1920 |
| actcatcaat | ccatcaagcc | atcagttcat | cacaccacac | acagcagtac | agcagaggag | 1980 |
| cactgcag | | | | | | 1988 |

<210> SEQ ID NO 2
<211> LENGTH: 2133
<212> TYPE: DNA
<213> ORGANISM: Oryza sativa

<400> SEQUENCE: 2

```
caccgcggcc gcccattgct atcttctacc gttcactggc agccatacca tttggcacaa      60
tggttgtcat atttgtcctg tgggctttca tctcttttcc tttggttcta ttgggaactg     120
tagttggtag aaattggagt ggtgctccca acaatccctg tcgtgttaag acaattccac     180
gtcctattcc tgagaagaag tggtatctta caccctctgt tatctcattg atgggtggac     240
tactccccct cggcagcatc ttcatcgaga tgtactttgt gtttacttca ttctggaact     300
acaaggtaaa gaaaacatat cagtgaacac taatgtgctt ctcagttctc acttctcaac     360
aaattatttt gctagaacag atggcattta cagtagatgt gtaccaacct aaaactcttt     420
ttaatttgat ggatagatag taaccctatt tctttggtat ttggcaggtt tattatgtat     480
atggtttcat gctgctggtt tttgttatcc tcataatagt caccatatgt gtcactattg     540
tgggtactta tttcttgttg aatgctgaga attaccattg gcaatggaca tcattcttct     600
ccgctgcatc tactgccttg tatgtctacc tatactcaat atactattat cacgtgaaga     660
caaagatgtc tggcttcttc cagacaagct tctactttgg ctacaccttg atgttctgcc     720
tcggactagg aattctttgc ggtgagcatt taaacttgta ttcattgtat ttcaaattgc     780
cacttggtct gttttgacac cacgtctttg gtttaggtgc tgttggctat ctaggatcta     840
ctctctttgt gaggagaatc tacagaaaca tcaaatgcga ctaaaattgct actctgaaca     900
tcaaatgtga ccaaagggct actccgttgc cgatagatcc tatcagcgaa gtgtgtgttg     960
ctggcgcagg tccattgtgg agtaatgctc ataagattct gatcaacttt tggaagctat    1020
acaggagatt gttctcccctt tgttttacct tttctttta tgtttttctt ttacttcatt    1080
tttcttcttg gagctggcct cataaatgta tacctcatta gttcaggaat tagtctcagt    1140
accgggaagt acatttagat tctcattttg tggtggcctc ttttggccag tagtaggata    1200
tcattgatga atattggtgc agtgtggatc caatccagtg gctagaattg cccctcttat    1260
gaatcgctat acatccaatt ttggcatagc cttgtagtat atgcaaacta atacattcaa    1320
gttagatata tatggcctga atgggtgaag ttctatttct tcccctgcag gtactgttga    1380
aacatgaatt cgacatgatt attatttagc ctttggtctg agttttcatc cttgctgaat    1440
tgtctctgtg tttacagcat cagaaatcaa gcgtacactg aaaatagaca aatgtgtcat    1500
ccacatctgt aatgttttgc ttgtttaggt accttgcttt atgatagtat cagcaaatga    1560
tttaagataa gataaagata tgctgctaac cagatggaca tcgtaacgtc gtatatctgc    1620
aggtttcatt gtacaggtgt acagaattta tatacatatt cgagtatata ggtatataga    1680
cacactggtg ttgaagacat caacttatta agttattatg tttatctcta cgcacattga    1740
gagcatatca acgtgtcata tcactggaca ctggatgacc ggccatagta gcactttcta    1800
gcgatcaagc ttagttgacg tttacgaagc aggcacgacg ctccaagcca ctaagctact    1860
cccacgtgac cagctcacgt gtcaccatcc tgcacgttca cggccccatc cacagcacac    1920
gtggcacggc ctcacgagcc acctggacgg ccgaccagcc ggccggcgag ctttaaaaag    1980
cagccccatg tcatttgctg attttgctga tcgatcaact catcaacccg tgcagcaatc    2040
catccatcca tagccgatct cagcttttcc attcgcattt ctgcttaatt agcttagcaa    2100
gcaacgaatt aactgcaaga gagagcgcca tgg                                 2133
```

<210> SEQ ID NO 3
<211> LENGTH: 2463
<212> TYPE: DNA
<213> ORGANISM: Oryza sativa

<400> SEQUENCE: 3

```
caccgtcgac actaactaag aatcaaatgc aacccaatat ggaaacctct gcagcaccgt      60
caatttgttt tggctcttgc agtgaaacca aaggaatttt gtgtcctggg ccctatccac     120
cacgtgggcc atgcagtaag atttccaacg tgagctcaca tgtccaaaac ggactccgga     180
cgagagagaa acaagcgttt tagtccaagt atgtccgggc tcacccaaac caagtccgaa     240
ctgaatctct tcttccttat ctttaaacta ttgttttgga aggtttcaat tcgtgggaat     300
ttttaagtgg aatccatatt aataataggc ttttacctcc attgcatttg tatatggagg     360
gcggtaactc gtgaaagtac atgagaccac gatcacacac atatatacat gacgacgaac     420
gtgaaatccc accagaagcc taacgtattg tttaagtagg tatatatata aatatattga     480
tagatttgca ctctacctct cttaagtgtg agtaagctag gtgctagaaa atttgagaac     540
tctttgtttt gtcgtatttt actgattcgg tctaacggct atctcactcc taattcctgt     600
atcaaatggt ttctcttacc acgtggatca attaggtaac gttttgagtt gcaccgttca     660
cttagacaga tagctaaacc ttcaaaccat cagaagaaat catggcggcg ttctggaaat     720
aagatgaaca gcggcatcgg cgcacgccgg agtcgagaga aaagcaggcc ggcgaagcgg     780
tacgcgcaaa aaaaaaaaaa aggcccaaac gtccaactgt ggcccagtcc aattgttcac     840
ttcagttcat ggcccatctc ctcctcccat atctccctga ctcaaccacg ctagccacca     900
accctagagc ggcacgaccg gcggcggcgt tgcggtggtg tttgcggcag cgtgttgcgg     960
cggtaacagc gagccagacg agcagcgatg cgcaaggcag caagtggcgg cgcggcgtgg    1020
gcaggcggcg acgcgccgcg cggcgcgcgc agctagctgc tagcagagca gcatcaaaca    1080
agcagcgcaa gcggcaagtg ccaagctagc accgagtcct cacttcatgt tccattcttt    1140
tttattatta ttattattat ttcagcaaca gatgatggga tttacaagaa ttgggctcat    1200
ttttttacag tcttgattta ctcatagatt agcggtgaag aagagaacaa cattgttaaa    1260
ttatcttgca agcgatttaa gtaattaaca cacttcaact gatgggagca taaatcaacc    1320
aaaaagacct tgatcctaat gatacctttt cttgataaat agttttctca aatcatagat    1380
gaagcaagga gggaatattt gttgaaggct ccaaatagag cgctaacttg gctattccaa    1440
agatattaga tggcaaggtt tggttgatac aaatatgcaa tataatcact acttttcat    1500
tgggaaggta cttcttcttt atggtttatt ttttaagtc atgtatatgt tgaataacta    1560
gtgtaaagat agtttttgtt ataacttatt agtactttga ggttgagcct atcctctatt    1620
tcaatcctga attttaccac tgtcatcagg tatgggtagc atccatttaa tttctcatcc    1680
tagtgataga gatcaacaaa gtcgttggac aggtagtgtt gccaggtgat catatatatg    1740
caagcgcggc tgccttctat agatgcatgg ccacagatct ccccagctca tcctctttca    1800
agaaggagct gaaaacgatt aatttaattt ccatcaaaac gataaaagat ggaaactgca    1860
ggcggccact gcatgcaccg gcctctgaac ttgtacgttt gtatgcatgt gatacaaagc    1920
tcaacacgtc agctgcgtcc atatgcatat ccgtctctca cacacgcata tataaattgt    1980
gcaggttgca aaggatgctt tcgctttcct tccttccctc cctgatgagc gatacttcga    2040
tatcgccagg agataataaa taaacacata agtacagtat tagtattact ccgtacttac    2100
gcgtgaagat ggatagcgat gatgcgttgg ctcgtgtgtc aattaggctc gatcgagttt    2160
```

```
gatcgttaag taagttcagt ttattgtttc atttgcacgg catgcatgtt tgttagatgt    2220
gtgatacatc tgattaatta tatatagtat ttcatatata tgtttctttt ttacgatgtt    2280
gattagttca aaataaacta taacaataga tcatatagaa agtatatgta tgtgtgtata    2340
tatatttatg tatgaacccg tgtagttaat taattatata tagctttgtt ttggcgtgcg    2400
aaaaatggag atatactgtg gaattagctg ccaggccgga ggggagaaat catcgtgcca    2460
tgg                                                                 2463

<210> SEQ ID NO 4
<211> LENGTH: 2035
<212> TYPE: DNA
<213> ORGANISM: Oryza sativa

<400> SEQUENCE: 4
caccgcggcc gcgggttaat gtagttcttg gactcacaaa aagtgccatg tgagcatatc      60
aagtcatcct cacatgcagc gatatgaatg aaatgaccat tctacccta tataccatat      120 agaaaagaat aaaaaaagaa acaaatgtt ttcacgcgtg tatgatcgtt ttacaattgt       180
cacttatgat tgctacaacc aagcactgat cgtataaatt cttttgtcgg ccaccctccg      240
caataatatt gggcatgggc tggcctgttt attttttcctg tttgtctttt ctttcttttc    300
tatatggtat ataatggtag aatagtcatt tcattgagga tgacttggca tgctcacgtg     360 gcatttttt tggtctaagg actatattaa cccaaatgat taatttagag acttgtttg       420 gacgatttga aatctcaaga actaaactga gctcaaaacg aaacttcaag gaccatatta    480
actattcacc ctagttttaa tcgcactcgt gcaaagtaag tattccctat gtccctaaat    540
ataagagatt ttggtttgat gtgatatatt tcatatctag attatcgta ttaggattta     600 tcatatctaa ccaaaatccc ttatatttag ggaggaggga gcactacggc gcaccgactg    660
accgacctat ggggcttacc catgagcccc gaagttggac gtgtcaggtg agatacgcgc    720
gtgtaccgat gccacaatat gtacgtatgg tcgatgctgc accgaggcta gcagcacgaa    780
agggcctcca taacctacgc ctagccctag cacgatggat ggcacagtgc gtgcccatcc    840
tgcatctgca tgggttagtg cgtgctacgc tgcgacggcg acgatcgatg tagcctagcc    900
ggtgtgtgca gtgcagtgca ggtcaggatt gccactatga ccaaaggatg cttgtgtgcg    960
atcaataatg gccgctcaat gtgtcatcgt acggtgacac accactcatc ctttgttgat   1020
ctgtggtgat cgacttgagt taatcggcaa ggcccagccc atggtttgag gtcagggcca   1080
ggctgaattt ggcccagtaa ttttggtttg agaagcccac ttcgtcacag cgtcaggccg   1140
aattactggc ccatggtgag cccatggcat ccattcccca tgattgacct tgtctttctc   1200
tttttctctc gatctcgaaa agatgagcag atactcgtaa ttaaaccgca acatctgcc    1260 acccatgtaa tgataacaat cgttaacaat gccatgcatc tcccgaagct tctgtgccta   1320
ctcatttgag tgcgagacct tcctaacatg tgtccccta acattgttta ctccctttgc    1380
cgccaaagtg gttactacac actccaaact tttgtggcag aagtacactc aaaagcgaaa   1440
ggtagcagaa cacatcaggc atccaaatta acaacaacac catttacaat cagacctgaa   1500
cacgttgatc ggcgacatca ggcgccgcac atggcaacga cacccgatcg atcaccaagt   1560
gtaaaaacta aagccgcatc caacttgtac tcgccaaaca gccaccgatc gatcgacgtt   1620
tcgatcgcct gtatcgacac actgatcgat ctgatcatga tcagtttcaa ctcgctgtgc   1680
ccacgtgtcg agagatcggc acgtgcctga gctctcagcc gctcataaat acacttgttt   1740
```

-continued

| | |
|---|---|
| agtagcaaca gtatactata gtagtcctct cctgtttggc ttttagcttg catcgatgga | 1800 |
| tggatggatg gatcgcatga gagggcttcg cgaaggtacg gaaccttaca caacgcgtgt | 1860 |
| cctttctacg tggccatcgt gtaggcgtct cgccatgcta cgtgtcccgg aggatgtctc | 1920 |
| gatgccaacc cttataaata ctgttccatt ccaatcccat cgccacacag ccagtgcaaa | 1980 |
| tctgatcgat caagataatc gagcaaaatc catcagagtt ctaacattcc tgcag | 2035 |

<210> SEQ ID NO 5
<211> LENGTH: 1948
<212> TYPE: DNA
<213> ORGANISM: Oryza sativa

<400> SEQUENCE: 5

| | |
|---|---|
| caccgcggcc gcgcgatttg gtcagcttct tggatggcga cttcttagaa gacatacagc | 60 |
| tgctccacgg tgtcgatgtc ttgtgggaag aactcgacgg agccgaggcg gcagcggtag | 120 |
| agcagccagg tcgctgccgc tccctgccgc tgttaccaac accgctcccc actgccgccg | 180 |
| gtgctgctcc ccaccaccgc tccggcaagg tgaaaaaag agaccggggg agagaaagag | 240 |
| ggagggagga ggaagaaggg aaggagaggg aggatgacat gtggggccca catgtcagtg | 300 |
| ggtcccactt ttttttaatt gtgtgtgtgg atgacatgtt ggtcctacaa attttttgttt | 360 |
| tttgattta ctctaattcc acataagtga catgtcgacg acatgtggta tgaagaccgg | 420 |
| gtcaacaccg ccatgtaggt gtcacatcag ccaaaaccgc ttgcaaaacc acccaggtag | 480 |
| tcaaattgca ccggttttcaa tagttcgggg agacatctta tccggttttc atgttaaggg | 540 |
| gtacgaatta gattcggccg atatttaagg gagtcaaagt ggactttttc ctgaccagaa | 600 |
| tgatgatgtt gtagactcgt ggcacttgag atatatctat atgaaattga attgtatta | 660 |
| attctccaga aaaaaaaatg aacttatagt atatttgagc ttgtctagtt tgtaccatgt | 720 |
| tactaaaact caatgccaaa agatggatat cgatggtag ctaacaaaac gtaaagttta | 780 |
| tcttaagaaa acaattttcta aagttaccaa actaggggcc tattcacttt gatgccattt | 840 |
| tcaaccttac caaattttgg taaagttgcc aaaaaagtgg ctacatttag tttgctgcca | 900 |
| aattttggta actatataag aaatcatgct aaattgccaa aattttggta atgccaaaat | 960 |
| tcagtaaggt ttttttcatc aaagttaaca aaccctatat gccacatttc cacttgttct | 1020 |
| atttgaaagt gtatagttac caaaattgaa tgagaactaa ggggaacgac aaaaattgtt | 1080 |
| tcaaaatga aattaattgt cgatcatgct attgtcgtgg attagtcaag ccttatttgg | 1140 |
| tctggattaa ttgtcgatca agtcattatc gcagattatc gatttatca tagcataatt | 1200 |
| taaacaaata tttatttaac aaatagttta acaagtgac aataaaagaa acctttttt | 1260 |
| caaaagtaaa cctatgctgg gaggcatgaa gcaataatc gacgataaca aaaatactct | 1320 |
| ttatcataaa tatttaacat atggaataag atttgattaa acttttaaaa atctcacaat | 1380 |
| caatttttg ttttaaataa atcaattaaa tatagtaagc ttaaaataca atacttgtaa | 1440 |
| cttttaaggc aaacttaagt tttaaggaat tattaatgat caaaattttt aaaattttca | 1500 |
| tataacttta ccataaacat taagtattcg taaaccactc aaagcaagca gtgagtgaac | 1560 |
| gtggcagcta ccgaactcat ctgttgaggc ccggcaagca agtaattccg atggaaatgt | 1620 |
| tgttcgagct tagcaactct tttgacgtgg acaaatacaa acacgcgtcc attctctgca | 1680 |
| cagccgacgt gccacgatgc atccagagat tcccccgcct tcgctcacgg cggcctcagc | 1740 |
| aagcgacacg tccgtgtcac acgcacgcac gcacgcatcg atcgttcgcc gctttatctt | 1800 |
| gtgcatataa atcgaaacga cgatgaggcc gcaggcagcg caagagctag cgcaagagct | 1860 |

```
agcttacacc gatcgagcag atcagacaga gttagctgca gagcagagtg tgttaaagac    1920
tagttgggac ttgggagagc catggaat                                       1948

<210> SEQ ID NO 6
<211> LENGTH: 1881
<212> TYPE: DNA
<213> ORGANISM: Oryza sativa

<400> SEQUENCE: 6
caccgcggcc gcgttttaga gttggacaca gttattaaaa agtaggtata attaaatagg      60
aaggggttgt gattaattga aaatggagg taaatgggaa aagtgaatgt tgaagggtca     120
agttgggaag gaaatgttgg tagagaagtt attatattta ggacaaatcc taaatgctaa     180
aagttattac attttggaat gaatggagca gtattttcct tagataatgg attaaaacct     240
gaccactaga ccaacaaaac tgtacacagt caatcatatt gagagttgat tttaaactct     300
caaggggacg tcccctcata atttacatgc tactcaaata attatgaaaa aaattgaaaa     360
gatatattaa catgtgatat attatttcac aaacatgcaa gtaaaattta acttttataa     420
gtcacaataa aaaattaca attagttaac atatattcat gatcaaattt gttttttttg     480
caacgtataa aaatcgaatt tgattttgca tgtttgtgga gtggtatatc gtatattaaa     540
ctatcttgtt aattttttta aaaaaaatt ataattattt aagcgacatg caaacagtga     600
ggagacatcc attcgagtgt ttagaacaat ttctccaatc atattatttt tcacgtacgc     660
attttttctt caagaattac ttttgtctct tttttctttt tttagaaaga gagggagatc     720
ctctcacatt tccatcaaga aatgaccggg ctacagcaat ttgaaacaaa caaccacaga     780
ccacgggaac atgcaaacat ctggcgccat cccaacaaaa gggtaaatat agccattttc     840
caaattccaa tacaactatg agtagtgcca tgtacgtgcc accactatct gcaaagcgat     900
atggctttgc tacatttca accaaaagtt caggaccaca ttgaccatgc gcagtacgtg     960
gtcattatac attcttctc ctcgaggtga tatcctccgg agggacgaag atatctctcg    1020
tttcatttca tgcatatcac ctaaatagtc attaaaaata tgaaaaaaaa aattaccaaa    1080
atagattagt atgaaatata ttagttcaca tacatgcaaa tcaaaattta acttctataa    1140
attgtaacaa aagtaacaaa tatatacgtg aatgcacgat aactattttc agtttaattt    1200
atccttttcg ttgcaacttg tagaagtcaa atttgatctt gcatatttgt ggattgagat    1260
atttcatatt aatctatgtt attattttt tcaattattt tgataactat ttagatgaca    1320
tgcaaataac aaggtgatat cgcctcgagg gatgaaattc cacatcccta tattcacatg    1380
tccacagcaa actagacttg cctaattaac cggtaatgtc gatcgaaacg atgacacatg    1440
ctctcgtcag ccatggagat gccattgcta caagcttcag tgaagatcag caatttctcc    1500
cctggtttgc ttgccgtcca aaaaaagat gtcccctagc tttgatcagt gcgcatgcat    1560
cgactctact acgtgtaaac tctacagagg cacgcctcat gagactttcc ttgatcagct    1620
atagcttcat cggtctgaac ccactcatga tgaactctct gaaactctcc ccgttccact    1680
aacaccaccc actaacatca tcataaaatg ttttgctccg ctcgtacacg caaagagacg    1740
aacacgtcgc cgcgcccgag ctcacggtgc gcctcaccta ctgcaaacct ctgcaaatgc    1800
ctataaatac accgacgagg cagcgatcac tctccattca cagcaacagc acatctcgca    1860
gcttaatttc aggtcgacaa t                                             1881

<210> SEQ ID NO 7
```

<211> LENGTH: 2118
<212> TYPE: DNA
<213> ORGANISM: Oryza sativa

<400> SEQUENCE: 7

| | | | | | |
|---|---|---|---|---|---|
| caccgtcgac | tagtgactac | caatgctcgc | ttcgcctgtt | tacctgcaaa | aaccaactga | 60 |
| catgtgggcc | ctcagtcaac | ttagtataaa | aatcaccatc | tagaattcta | gggttttctt | 120 |
| ccttccctcc | cacccaccat | ctagaatttt | attgaatcgc | caccaccctc | ccacccacca | 180 |
| gttgtcaccg | gtggccccac | cctctagccg | gcgactttca | cagacgccac | gggaggagca | 240 |
| accgaggaag | ctgcgaacgc | cgccgcctcc | tacccttct | gcgccgagct | cccacctccg | 300 |
| gtcgtcgaag | tcctccaacc | gtcaaccgcc | agcctgccac | accttcctcc | agccgcgcct | 360 |
| ccaccatccg | cttgcttggc | tgcctcccac | ctctggtcgt | cgccgcctcc | tacctccact | 420 |
| gcgccgagct | cccctccggc | cgagaatttt | attgaactat | aacaggtaaa | caggcatgcc | 480 |
| cgcgggcaca | taacacccac | cggcgacaag | tatagacaat | gttccttacc | catcatgtag | 540 |
| tagcgggtat | gtccgcggac | atgaattacc | tcacggacat | gggcaccctt | ggtgcccgac | 600 |
| tgcaatccct | aattgggagg | tcttgagttg | agaaacgacg | gcacgatgca | cgagaaagac | 660 |
| aacggcaatt | accggcttac | ccttgagaat | cggtacctcc | tcattcccac | cttgcgctac | 720 |
| caccatgtaa | ccaaactctg | ttagccctct | gatttgattg | gatggacagc | tcaaattact | 780 |
| ttattctctc | tcctcaagga | tggtaaatca | gctcttaaga | ttgaggcata | aattatccaa | 840 |
| aaagaaaaaa | tagattgacg | catacgacag | aaactatact | catagttgag | ggatgtaaag | 900 |
| tgcacttttt | cacaaaagaa | cacacctacc | tcaccggccc | aactataata | agtcaccggt | 960 |
| ctttctatag | cccaatctgt | actggcaggc | ttgtacgagg | ttctctgtaa | ggaataagtt | 1020 |
| ctcttgaagt | ccctcatgtg | cctagtctaa | ctttcgtcct | tacaaaacca | atgcccttgg | 1080 |
| cagtattcat | ctaagttttg | gtagcgggac | gcctacgtgc | gtactttaaa | taggtcttcg | 1140 |
| tcccacgtag | cattgacttg | gcgcttacat | gatagtttgt | tccggaaaaa | aatataaaat | 1200 |
| gtgcaaaatt | gaggatgccc | cgttcaaact | ccaaatcctg | ttcaccggtg | gatcgaggag | 1260 |
| atagaggtag | aaagggtgag | gtggaggaag | tgggaccgac | tgacatgtga | gtccaattat | 1320 |
| tttgtatcat | cttgtttcac | tgatatatgg | gccccacata | ttttgttttc | tttttttagt | 1380 |
| tttcaatttt | gctatttaa | tcaaactgtc | acgtaagcgc | cacgttatta | ccacatgaga | 1440 |
| tgaacatcta | aacaaagaag | tcatgtatgc | gccatgtcag | tcaaaatcgg | ggaaaatact | 1500 |
| tgttgtgttt | ggctgcacta | gctgccgcaa | cgggcaatga | ctggtcagct | gcggctgcag | 1560 |
| cagttgtgaa | tggctgcagc | tggcagccgg | tttgaattgc | cgcagccaca | gcggctgcag | 1620 |
| cagcaagtcc | ctccgaacag | agccactatt | gaggaatctc | gtttcaactg | gttttataaa | 1680 |
| ttgggggatg | ggctgttttg | aattttcggt | ttgagggacc | aaaagtaaac | ttattcctct | 1740 |
| ctgtaaacat | ggcaccaaca | tccgaaccaa | tcgatactca | cagtccgcac | ggcccaccag | 1800 |
| gcccagacac | ctcggactct | caaagcggac | gggaatgttc | aggaaaacgc | gacaagagcg | 1860 |
| gagaaccccg | cggcgtcgtc | gcgaagctcg | aacaaccaa | cggcggcgca | cgctgtcccg | 1920 |
| aagcttcgcc | acctttcccc | acccttccac | accgcccgtg | gcgtgagcta | taaaatggcg | 1980 |
| ccgcgcactc | gcctgttccc | cgcaattgaa | gcaagcaatc | aagcgacgat | aattagagca | 2040 |
| ctcgcgacct | ctccgacgat | ctccagctca | ctgcttttag | gttctcaaac | tctgatttcc | 2100 |
| tctctactct | gtccatgg | | | | | 2118 |

<210> SEQ ID NO 8
<211> LENGTH: 1976
<212> TYPE: DNA
<213> ORGANISM: Oryza sativa

<400> SEQUENCE: 8

```
caccgcggcc gctggattca ttggattggg ccggttgtag gaaataact catggcactg      60
tgccaggtgc caggtcgttt attctaagcg agaatcggca gtgtcaggct ctggaaaatg     120
aacgaaaga gacgacgaga gaagccatcc ttccctagat acacgactgt tactacaggc     180
cggcttatcc agcaacatcc aacgagacga gacagggagg gtataaaaaa aaaaggaaca     240
cccccatgct ctcgtcactt ttgattgtgt ttagtctcct ttaaacttta aaaaaatctg     300
tcacattaaa tatttagaca cctatataga gcattaaata taaatgaaaa aataattac      360
acagttcaca tgtaaattac gagatgtatc ttttgagcct aattacatta tgatttgata     420
atgtggtgct acagtaacca tttgctaatg acggattaat taggcttaat aaattcatct     480
cgcaatttat aagaatctgt aatttatttt attattagtt tacgtttaat attttaaatg     540
tgtgttcata tacttttaaa aaaatagctg tggaactaaa cacggccttt gtcagttcta     600
cggtagttca gcccgtcatg tagttttaaag accaccggta tgatcgtaac tttgtcagag     660
gaggaagagt tggtttttat atcacgttca gtttgagcgt tgcttttgga agcccagcac     720
gcaaagcggc tcgtccaact tttgatgtta gcgagggaag ggtaaagaac gtgcaaagag     780
cagaaaacga aatgccgatg atattctata gtggcgagtg cgcctgcaga ctacactcga     840
tataccgtgg gaactacgga aagcggcaca caccgggact acactcgata tgcacacaag     900
tcgcagacca cccccccccc ccccccccca atacacagtt tgcatgtgga gttctgcagt     960
gtggcgtcag ggtggcatgg cagaaaacgc agatggctgg cacggaactt ggcaaacagg    1020
atggagagac ggcaccgtcg tgattccacc tgttttttgga acgccaccct cggtttcatg    1080
agagatccgc gagccacaga ttgattgatc agatcagccg tgtcggtgtc ggctgggaat    1140
ccggcaaccc gagcggtcgg tggcggcgct ccccgcgcgg ctcgccgaga gctccgtgtg    1200
cgcccgcagc cccgcactac caaaatttgc ctcatcatgc cacaactcaa attagccaaa    1260
gtttaactta gttagacatt cgtttgtttg gtgccacact tttgataaga ttccttcacc    1320
gtgatgtggg tcccacatat cattggcaca taaaagtgtg gcaagtttac tctactatgg    1380
ctaaagtgtg gctttaattt tgttggccac atgttagaca tgttagctaa ataaagtata    1440
gcaagttttg ataatgtgag tatgccaact aaacaaccta tacgactacg accggcgcgg    1500
tgtgtcggcc cggctctctt gatggaaacg ggtgggccat ctcggcgaac gactcacttt    1560
gtgtcggcag atcagcgggt tcgtcggccc gggttctttta tgccctttgg gcctctctcg    1620
cacatgacgc ggcctcgtgt tgtgaaaact cagcccgata ggacggatta taggcctcca    1680
atcggcggga ttcttcttt cttaagatga aaatttatag aggcaggttc acgaacgtat     1740
acatggatga ttatcggggt cacacgacat gtgtccgcgt cacactgtca cgtaagctca    1800
caagaaagaa ctaaacaacg agaagtgcct cttaacactt ggacatctct ccagctgcct    1860
cgtcgcgccc ggacacttcc agttgcagca taaaagaag ccagacatcc tcctcttcct     1920
aacttcagct tggctcgcgg cgggacgcca ccagagaaga ggaacaagtc gacaat        1976
```

<210> SEQ ID NO 9
<211> LENGTH: 2047
<212> TYPE: DNA
<213> ORGANISM: Oryza sativa

<400> SEQUENCE: 9

```
caccgcggcc gcgatcacga atatcaacgc cattggatct tatatacggt ggaacccatt      60
agtacatcag gagttcaaaa ccacgaaaac cttataataa aatgagtaaa tttcatatct     120
attatgatat gagcgaacag atttggcacg agaaacataa tcacaaccat tgtggttgaa     180
gttttactaa ttcacaccgt taactaaatt gatatactct tgttttgaaa ttttaaaaag     240
ctttatatac acgattagat ataatattta tatgatgaat aaataactta taaattagat     300
aaaataatta ataatgtggt ttgtgaaact ttatagttat aatagctagg ggttatgtat     360
cacgtgccaa aacccattag ttttgtatat ttggggttat ctaaaattta ctcttttatt     420
aataatcaat aggaaggagt aaagagaacc attgaattcc cactcaaggg gtgacaaaat     480
tcactaaaaa ctaaccacat aatcgcgttt tgcgcgactt tgatcctgt ttattgtata      540
tggtctatta gtttaccta gctcttaata aggttttgat aaaaagttaa tttgtttatg      600
aagtatctat tgttctagcc aactataaat atagctacta atacctccgt ttcaggttat     660
aagactttct agcattgccc acattcatat agaggttaat gaatctaggc acatatatat     720
gtttagattc attaacatct aaataaatgt gagcaatgct agaaagtctt acattgtaaa     780
actgatggag tatatgttta taagaggaat cactagaagc atcatctttc ttctctttat     840
ttcctttctt tttgtatgta tcatatgttt agtaggagat gccagaaacc tccaaaaaaa     900
attccatata tttagcccat ttatgatttt ttttaataca tgctctcttc gatccaaga      960
ccattattta tccaagctct ttatcagacg gctaacatat ttttgatgat atagcacatc    1020
ctcgtataag aaggcttgct gctttcacta tataagataa gattcagtca cgtaacatct    1080
aatcccaata taataaaata ataatgataa atatttaaa aattaaaatt gaaacataat    1140
ataagatatg gtcaaacttg aaatgatctt caaaactaat attaagctta taatttctcg    1200
tatgttataa gttttataac aaagaaatta taattatata aaaataaatt caaatatcaa    1260
ttcaataatg taacttttag caaataaaat tcaatttata ttatagtatt ttttttgtta    1320
aataatttaa aagttcaatc ctaaaacaca tgtgcgtctt atattataga atgaagaagt    1380
atatatattt tttaatcgaa aggaaaaaat atgcatctcc acggaggaat aaatatatcc    1440
cgcaactaat gaagtgtcta aactctaaac atatgtcacc accaccacga aagtacgaat    1500
aagtcttccg agtagtagca aatatagtat gtttcatcta agtatttcat ctaagcacga    1560
tagaaatttt ttaagtattt tatcaaaatt tggtaagaaa ctaaacagtg cacataattg    1620
gcaactttaa aaaaaatggt atggtttaaa atgacatcaa tctgaataag tcataaacgt    1680
gacaataatt ttttcaaaaa aaaacacagg gaaaatgttg tactcgatca tggtaaattt    1740
tctatataca ttctgaaaat atatacggcc gtatatacgc ttgtatgcat acggtcagac    1800
gtacacgtat gtcgtacacg caaagtataa agtaaccgaa tggcctgtcc cctttctagc    1860
cgcttccagg cgacgccgtg gcgcgcccctc ctgtcgccac gtgtctcgcc ggcgccacct    1920
cgctcccgcc ccttccagac gcttcgctgc cgcaccccca ataaatcgcc gccgtctccg    1980
gccacctcct ctccctctcc atctcaggca aggcaaaccg ctcaactctc tccgctccaa    2040
actgcag                                                               2047
```

<210> SEQ ID NO 10
<211> LENGTH: 2051
<212> TYPE: DNA
<213> ORGANISM: Oryza sativa

<400> SEQUENCE: 10

```
caccgcggcc gcggttgcat tacactgaca gacagtcaag taccgtacca ctctttctcg    60
ttctttcctt gaccggttca aatgtactgt gccggtacaa acaaacaaac gaacaaagta   120
tgaattccaa gcctctaggt tctaactact catccatcac ataaaaaaac aataacttga   180
attccaaatc catgaccatg aagatatcct ttcatgcatt cacacatttc aggacctcct   240
ttggaatagg ggaattgtta gaggattata caattccaac taattaacgg catggtacgc   300
tgtcaattgt tcggtactac tccatgtcca tgtccatgtc catgtccagc agaaattaag   360
tcatgtcagt ttcagtgctc tttgttagac tactgtattt tgtaagcact caacactaac   420
cacaagagta gcagagacct tggtggtgga ctactccgcg tgaaagtcag taggccggcc   480
gttagtgtac aagagatttg cttgattttc ctctgcatgt ccggttgtcc accctctgaa   540
atggggaaca gagacagtag ccatagacgt ctcgtcaacg cagaggcgag cgaccattc   600 aagtcgagtc gtccaccgag gagaccacac acctcatctc cctgatcaat tggctgagca   660
gttcgctata gccagtgctt gttccatttt aaaatataag agattttaaa cgtggatata   720
acatattata atattttat ttaaattcgt aatattaaaa tatatcttat ttatttaaaa   780
ttatttatat tttggacgga gggagagcta ggtttgcgga aattttcaat agcctcatgg   840
gcagacaagt taaagcaagt tatctaagag aaaaggttaa agtagttaca gtcacattat   900
aaagttctgt taaacaactt gcagcagatt cggcccatct gcaaagtgcc attgttaagc   960
agcatatact aatactccta ctatgtgatt tgctatttga cgcgtgggcc tactagccgt  1020
acgaaataaa gtcgtattgg acgcgtagct atgttgcttc tacgtctgct tcgtcatggt  1080
tcgtttcgtt cgtacgcagg gaatcaagca tatgataacc actggaatag taacggtaat  1140
agcaatggct agagggagct ccagtggcct gtgcgaagca tacggaatcc gaatagcagc  1200
aacctccttc agagatagac gtactgtacg tacttgccat caactaagca gtttcagtga  1260
aacttccacc atgctttaat gctttgcctg atcccagatt cccagacttc agtgcaacac  1320
ccgggaaaat tcggactcgc cgcactcgct gcaactccta gcatgtgttt agattggccc  1380
aaagtttaga atttggttga aattaaagac gatgtgactg aaaagttatg tgtgtatgaa  1440
aggtttgatg tgatggaaag ttgaaagttt aaaaaaaaaa actttggaac acacagtagc  1500
tcgcaaggcg ccattccgcc gaattgctta ggcaacaggc tacttgcatg ggagttcgtt  1560
tttgcgtgtg cgattcggtg cggttgcggc accgggcttg atggattggg tagtggccga  1620
ggccgatggc tctccggcaa tttgttcggc ccagccgcgc gtggcgagac cgtgggcgtg  1680
ggagttcacg cacgcaggga gcgggtgtgg gttgccgggc taaaaagccg ccggcaacag  1740
ccacgtcccg ccgcgcgtcg cacgtccgcg ccacgaggca ccgacctatc cccgcctcgc  1800
gcgccaagcg ctccacgcgc cgcccagcgc gcaaggccc gcaaatacgt ggatccccca  1860
cggcgcaacg ccgcaaataa tttacccgca cgcaagcctg cacgcgaacg ttcgcgacac  1920
ttcgtaccaa tccattgtcc gtcgaacgcc agaactattt aaccaagacc aggcgcgcga  1980
agagcgaacc gacgctatag cttcagctac gtagccgttg ttcatcactc actcaactca  2040
gctcactgca g                                                       2051

<210> SEQ ID NO 11
<211> LENGTH: 31
<212> TYPE: DNA
<213> ORGANISM: Artificial Sequence
<220> FEATURE:
<223> OTHER INFORMATION: RP2H Forward Primer
```

-continued

<400> SEQUENCE: 11
caccgcggcc gctctctgtg gctgttgtgt c        31

<210> SEQ ID NO 12
<211> LENGTH: 24
<212> TYPE: DNA
<213> ORGANISM: Artificial Sequence
<220> FEATURE:
<223> OTHER INFORMATION: RP2H Reverse Primer

<400> SEQUENCE: 12
ctgcagtgct cctctgctgt actg        24

<210> SEQ ID NO 13
<211> LENGTH: 31
<212> TYPE: DNA
<213> ORGANISM: Artificial Sequence
<220> FEATURE:
<223> OTHER INFORMATION: RP9H Forward Primer

<400> SEQUENCE: 13
caccgcggcc gcccattgct atcttctacc g        31

<210> SEQ ID NO 14
<211> LENGTH: 26
<212> TYPE: DNA
<213> ORGANISM: Artificial Sequence
<220> FEATURE:
<223> OTHER INFORMATION: RP9H Reverse Primer

<400> SEQUENCE: 14
ccatggcgct ctctcttgca gttaat        26

<210> SEQ ID NO 15
<211> LENGTH: 30
<212> TYPE: DNA
<213> ORGANISM: Artificial Sequence
<220> FEATURE:
<223> OTHER INFORMATION: RP10H Forward Primer

<400> SEQUENCE: 15
caccgtcgac actaactaag aatcaaatgc        30

<210> SEQ ID NO 16
<211> LENGTH: 25
<212> TYPE: DNA
<213> ORGANISM: Artificial Sequence
<220> FEATURE:
<223> OTHER INFORMATION: RP10H Reverse Primer

<400> SEQUENCE: 16
ccatggcacg atgatttctc ccctc        25

<210> SEQ ID NO 17
<211> LENGTH: 31
<212> TYPE: DNA
<213> ORGANISM: Artificial Sequence
<220> FEATURE:
<223> OTHER INFORMATION: RP4 Forward Primer

<400> SEQUENCE: 17
caccgcggcc gcgggttaat gtagttcttg g        31

<210> SEQ ID NO 18
<211> LENGTH: 26

<212> TYPE: DNA
<213> ORGANISM: Artificial Sequence
<220> FEATURE:
<223> OTHER INFORMATION: RP4 Reverse Primer

<400> SEQUENCE: 18
ctgcaggaat gttagaactc tgatgg                                        26

<210> SEQ ID NO 19
<211> LENGTH: 30
<212> TYPE: DNA
<213> ORGANISM: Artificial Sequence
<220> FEATURE:
<223> OTHER INFORMATION: RP7 Forward Primer

<400> SEQUENCE: 19
caccgcggcc gcgcgatttg gtcagcttct                                    30

<210> SEQ ID NO 20
<211> LENGTH: 28
<212> TYPE: DNA
<213> ORGANISM: Artificial Sequence
<220> FEATURE:
<223> OTHER INFORMATION: RP7 Reverse Primer

<400> SEQUENCE: 20
attccatggc tctcccaagt cccaacta                                      28

<210> SEQ ID NO 21
<211> LENGTH: 31
<212> TYPE: DNA
<213> ORGANISM: Artificial Sequence
<220> FEATURE:
<223> OTHER INFORMATION: RP8 Forward Primer

<400> SEQUENCE: 21
caccgcggcc gcgttttaga gttggacaca g                                  31

<210> SEQ ID NO 22
<211> LENGTH: 28
<212> TYPE: DNA
<213> ORGANISM: Artificial Sequence
<220> FEATURE:
<223> OTHER INFORMATION: RP8 Reverse Primer

<400> SEQUENCE: 22
attgtcgacc tgaaattaag ctgcgaga                                      28

<210> SEQ ID NO 23
<211> LENGTH: 28
<212> TYPE: DNA
<213> ORGANISM: Artificial Sequence
<220> FEATURE:
<223> OTHER INFORMATION: RP10 Forward Primer

<400> SEQUENCE: 23
caccgtcgac tagtgactac caatgctc                                      28

<210> SEQ ID NO 24
<211> LENGTH: 25
<212> TYPE: DNA
<213> ORGANISM: Artificial Sequence
<220> FEATURE:
<223> OTHER INFORMATION: RP10 Reverse Primer

<400> SEQUENCE: 24

```
ccatggacag agtagagagg aaatc                                          25
```

<210> SEQ ID NO 25
<211> LENGTH: 31
<212> TYPE: DNA
<213> ORGANISM: Artificial Sequence
<220> FEATURE:
<223> OTHER INFORMATION: RP11 Forward Primer

<400> SEQUENCE: 25

```
caccgcggcc gctggattca ttggattggg c                                   31
```

<210> SEQ ID NO 26
<211> LENGTH: 28
<212> TYPE: DNA
<213> ORGANISM: Artificial Sequence
<220> FEATURE:
<223> OTHER INFORMATION: RP11 Reverse Primer

<400> SEQUENCE: 26

```
attgtcgact tgttcctctt ctctggtg                                       28
```

<210> SEQ ID NO 27
<211> LENGTH: 31
<212> TYPE: DNA
<213> ORGANISM: Artificial Sequence
<220> FEATURE:
<223> OTHER INFORMATION: RP3H Forward Primer

<400> SEQUENCE: 27

```
caccgcggcc gcgatcacga atatcaacgc c                                   31
```

<210> SEQ ID NO 28
<211> LENGTH: 24
<212> TYPE: DNA
<213> ORGANISM: Artificial Sequence
<220> FEATURE:
<223> OTHER INFORMATION: RP3H Reverse Primer

<400> SEQUENCE: 28

```
ctgcagtttg gagcggagag agtt                                           24
```

<210> SEQ ID NO 29
<211> LENGTH: 31
<212> TYPE: DNA
<213> ORGANISM: Artificial Sequence
<220> FEATURE:
<223> OTHER INFORMATION: RP8H Forward Primer

<400> SEQUENCE: 29

```
caccgcggcc gcggttgcat tacactgaca g                                   31
```

<210> SEQ ID NO 30
<211> LENGTH: 25
<212> TYPE: DNA
<213> ORGANISM: Artificial Sequence
<220> FEATURE:
<223> OTHER INFORMATION: RP8H Reverse Primer

<400> SEQUENCE: 30

```
ctgcagtgag ctgagttgag tgagt                                          25
```

COLD- AND WATER-INDUCIBLE PROMOTER FROM RICE

FIELD OF INVENTION

The present invention relates to the field of plant molecular biology, more particularly to nucleic acid sequences useful for driving and/or regulating expression of an operably linked nucleic acid in plants.

BACKGROUND OF INVENTION

Background description includes information that may be useful in understanding the present invention. It is not an admission that any of the information provided herein is prior art or relevant to the presently claimed invention, or that any publication specifically or implicitly referenced is prior art Gene expression is dependent on initiation of transcription, which is mediated via the transcription initiation complex. Gene expression is also dependent on regulation of transcription, which regulation determines how strong, when or where a gene is expressed. Said regulation of gene expression may be mediated via transcriptional control elements, which are generally embedded in the nucleic acid sequence 5'-flanking or upstream of the expressed gene. This upstream nucleic acid region is often referred to as a "promoter" since it promotes the binding, formation and/or activation of the transcription initiation complex and therefore is capable of driving and/or regulating expression of the 3' downstream nucleic acid sequence.

Genetic engineering of plants with the aim of obtaining a useful plant phenotype, often involves heterologous gene expression, which is generally mediated by a promoter capable of driving and/or regulating expression of an operably linked heterologous nucleic acid. The phenotype of the host plant only depends on the contribution of the heterologous nucleic acid, but also on the contribution of the specific expression pattern of the chosen promoter determining how, where and when that heterologous nucleic add is expressed. Accordingly, the choice of promoter with a suitable expression pattern is of crucial importance for obtaining the suitable phenotype.

Genetic engineering technology has led to the development of many transgenic plant species and varieties. Advances in genetic engineering have provided the tools to transform plants to contain and express foreign genes where an exogenous nucleic acid molecule such as a gene from a heterologous or native source can be incorporated into a plant genome. The incorporated gene can be expressed in a plant cell to exhibit the added characteristic or trait.

Promoters are non-coding polynucleotides that comprise the 5' regulatory elements which play a crucial role in expression of genes in living cells. The promoter controls expression of the gene of interest and thus affects the characteristic or trait conferred by the expression of the transgene in plants.

For production of transgenic plants with various desired characteristics, it would be advantageous to have variety of promoters. It is known in the art that multiple traits can be incorporated into crop plants using gene stacking. It is often desired to modulate or control each gene for optimal expression when introducing multiple genes into a plant leading to a requirement for diverse regulatory elements.

Numerous promoters which are active in plant cell are reported in various literatures. They are useful tools for expression of desired peptides in transgenic plants or alternatively for silencing genes or gene families.

These include the nopaline synthase (nos) promoter and octopine synthase (ocs) promoters of tumor-inducing plasmids of *Agrobacterium tumefaciens* and the caulimovirus promoters such as the Cauliflower Mosaic Virus (CaMV) 19S or 35S promoter (U.S. Pat. No. 5,352,605), CaMV 35S promoter with a duplicated enhancer (CaMVE35S, U.S. Pat. Nos. 5,164,316; 5,196,525; 5,322,938; 5,359,142; and 5,424,200), and the Figwort Mosaic Virus (FMV) 35S promoter (U.S. Pat. No. 5,378,619). These promoters from viral sources and such numerous others have been used in the creation of constructs for transgene expression in plants.

Constitutive promoters are known to drive gene expression in most transgenic engineering. Currently used constitutive promoter is the 35S promoter or enhanced 35S promoters (the "35S promoters") of the cauliflower mosaic virus (CaMV) of isolates CM 1841 (Gardner et al., 1981, Nucleic Acids Research 9, 2871-2887) CabbB-S (Franck et al., 1980, Cell 21, 285-294) and CabbB-JI (Hull and Howell, 1978, Virology 86, 482-493); the 35S promoter described by Odell et al., (1985, Nature 313, 810-812). Yet, promoters derived from viral source are less preferred for the transformation of host plant species, as infection of the plants with the virus may cause silencing of the transgene (Seemanpillai et al., 2003, Mol Plant Microbe Interact. 16(5); 429-438; Al-KafFef al, 2000, Nat Biotechnol 18:995-9). Also De Both Michiel Theodoor Jan found that the activity of the CaMV 35S promoter in transgenic plants was sensitive to abiotic stress. (WO 2007069894 A2)

Although constitutive promoters can improve resistance of transgenic plants to abiotic stresses, they are known to cause stunted growth and reduction of yield in transgenic plants. Another group of promoters called inducible promoters are known to direct transcription when they are induced by external stimuli such as chemicals, stress, or biotic stimuli. These inducible promoters that are expressed only when exposed to stresses is gaining importance in the art. There is a need for novel inducible promoters which are capable of controlling the expression of genes in a plant cell when exposed to external stimuli.

INCORPORATION OF SEQUENCE LISTING

The sequence listing contained in the file named 'Sequence listing', which is 32 kilobytes (as measured in MS Windows®) and located in computer readable form on a compact disk created on 29 Mar. 2017, is filed herewith and incorporated herein by reference.

SUMMARY OF THE INVENTION

This present invention relates to isolation and derivation of nucleic acid sequences from monocot plants, preferably rice that are capable of driving and/or regulating a stress induced expression of an operably linked nucleic acid. The present invention also is directed to the use of the isolated nucleic acid to drive and/or regulate a stress-induced expression of an operably linked nucleic acid.

One embodiment of the present invention provides isolated nucleic acid nucleic acid sequences having (a) a nucleic acid sequences as set forth in SEQ ID NO 3 or SEQ ID NO 6 or SEQ ID NO 7 or SEQ ID NO 9 or the complement thereof, or (b) a nucleic acid having at least 90% sequence identity in a continuous stretch with any of the DNA sequences as given in SEQ ID NO 3 or SEQ ID NO 6 or SEQ ID NO 7 or SEQ ID NO 9 or (c) a nucleic acid sequence which hybridizes as given in SEQ ID NO 3 or SEQ ID NO 6 or SEQ ID NO 7 or SEQ ID NO 9 or (d) a fragment of any of the nucleic acids as defined in (a) to (c), which fragment is capable of driving and/or regulating expression in cell wherein said nucleic acid sequences can be an inducible promoter.

In an embodiment, the isolated nucleic acid sequence of the present invention can be selected from the group consisting of nucleic acid sequences as set forth in SEQ ID NO 3 or SEQ ID NO 6 or SEQ ID NO 7 or SEQ ID NO 9 or the complement thereof where said nucleic acid sequences can be an inducible promoter. The nucleic acid sequences can be induced by stress such as abiotic stress including but not limited to water, cold, heat and/or salinity or a biotic stress such as by a virus, bacteria, or fungi.

In an embodiment, the isolated nucleic acid sequences of the present invention having nucleic acid SEQ ID NO 6 can be expressed under salt, water, heat and cold stress. In yet another embodiment, the isolated nucleic acid sequences having the nucleic acid the nucleic acid SEQ ID NO 7 can be expressed under water, salt and cold stress. In another embodiment of the present invention, the isolated nucleic acid sequences having the nucleic acid SEQ ID NO 9 can be expressed under water and salt stress In some embodiments, the present invention provides isolated nucleic acid sequences that are derived from monocotyledon crops. In an embodiment, the monocotyledon crop can be a rice crop.

In another embodiment, the present invention provides a genetic construct having the isolated nucleic acid sequences of the present invention and a heterologous nucleic acid sequence operably linked to said isolated nucleic acid sequence. The heterologous nucleic acid sequence according to an embodiment can be a beta-glucurodinase (GUS) gene.

In an embodiment, the present invention provides a vector having the genetic construct of the invention. In one embodiment, the vector can be an expression vector or a transformation vector. In another embodiment, the present invention provides a plant cell having the genetic construct of the present invention. In yet another embodiment, the present invention provides a transgenic plant having the genetic construct of the present invention stably incorporated into its genome. The transgenic plant according to one embodiment can be a monocot plant, such as rice plant.

In an embodiment, the present invention provides a method for driving and/or regulating expression of a nucleic acid of the present invention in a plant including the steps of:
  a) subjecting a transgenic plant having the genetic construct having nucleic acid sequence of isolated nucleic acid of the present invention operably linked to a GUS gene to a stress condition such as water stress, heat stress, cold stress and/or salinity stress; and
  b) investigating the expression of said nucleic acid sequence patterns in the plants by observing the GUS stained plant tissues; and
  c) selecting the plants displaying GUS staining;
where the nucleic acid SEQ ID NO 6 can be expressed under salt, water, heat and cold stress; SEQ ID NO 3 and/or SEQ ID NO 9 can be expressed under water and salt stress; and SEQ ID NO 7 can be expressed under salt, water and cold stress.

In an embodiment, the plants can be subjected to water stress by withholding water to the plants for about 1 to 14 days. The plants can be subjected to heat stress by keeping the plants at a temperature of about 35° C. to 42° C. for about 2 to 8 hours each day for about 2 to 6 days according to an embodiment of the present invention. The plants can be subjected to salt stress by irrigating the plants with a solution containing about 100 to 200 Mm NaCl for about 2 to 12 hours in an embodiment of the present invention. In another embodiment, subjecting the plants to cold stress can be by keeping them at a temperature to about 4° C. to 8° C. for about 2-8 hours.

In an embodiment, the present invention provides a method of producing a transgenic plant including transforming a plant cell with a nucleic acid sequence of interest operably linked to a promoter of the present invention, or transforming the plant or plant cell with expression cassette or transformation vector or expression vector having the genetic construct of the invention.

The present invention therefore provides a method for regulating stress in plants including transforming a plant cell with a nucleic acid sequence of interest operably linked to a promoter of the present invention, or transforming the plant or plant cell with an expression cassette or a transformation vector or an expression vector having the genetic construct of the invention and contacting the plant or plant cell with a substance or organism that induces the expression of the promoter.

BRIEF DESCRIPTION OF THE ACCOMPANYING DRAWING

FIGS. 1A-1B: FIG. 1A is a graphical representation of gateway entry vector pENTR-D-TOPO and destination vector pMDC164 useful for expression in plants of a beta-glucurodinase (GUS) gene under control of any one of the promoters according to the invention. FIG. 1B is a map of the vector RP 2H promoter cloned in pMDC 164.

FIGS. 2A-2E: is a digital image exhibiting expression pattern of RP2H (SEQ ID NO 1). GUS staining is visible in FIG. 2A root tissue, FIG. 2B leaf tissue, FIG. 2C panicles, FIG. 2D lemma and palea and FIG. 2E anthers.

DETAILED DESCRIPTION

Definitions

Figure 1A:
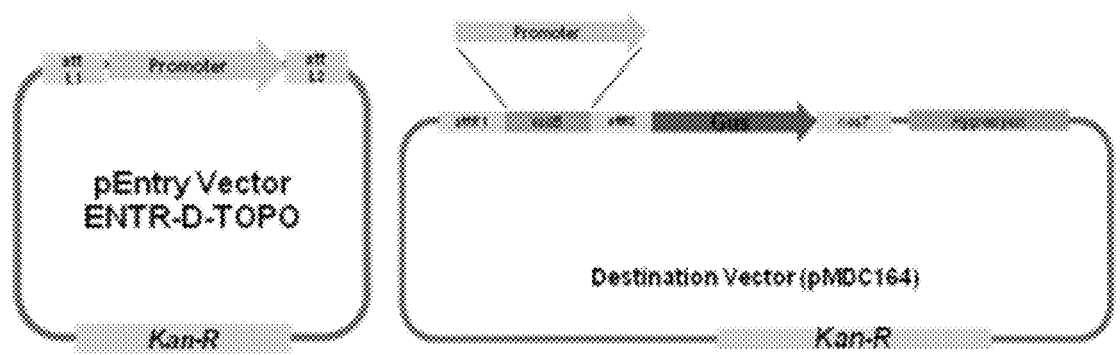

The term "promoter" as used herein is taken in a broad context and refers to regulatory nucleic acid sequences capable of effecting (driving and/or regulating) expression of the sequences to which they are operably linked. A "promoter" encompasses transcriptional regulatory sequences derived from a classical genomic gene. Usually a promoter comprises a TATA box, which is capable of directing the transcription initiation complex to the appropriate transcription initiation start site. However, some promoters do not have a TATA box (TATA-less promoters), but are still fully functional for driving and/or regulating expression. A promoter may additionally comprise a CCAAT box sequence and additional regulatory elements (i.e. upstream activating sequences or cis-elements such as enhancers and silencers). A "promoter" may also include the transcriptional regulatory sequences of a classical prokaryotic gene, in which case it may include a −35 box sequence and/or a −10 box transcriptional regulatory sequences. Preferably, the promoter is free of sequences (such as protein encoding sequences or other sequences at the 3' end) that naturally flank the promoter in the genomic DNA of the organism from which the promoter is derived. Further preferably, the promoter is also free of sequences that naturally flank it at the 5' end. The promoter may comprise less than about 2 kb, 1.6 kb, 1.2 kb, 1 kb, 0.8 kb, 0.5 kb or 0.1 kb of nucleotide sequences that naturally occur with the promoter in genomic DNA from the organism of which the promoter is derived. The invention encompasses an isolated nucleic acid as mentioned above, capable of regulating transcription of an operably linked nucleic acid in a plant or in one or more particular cells, tissues or organs of a plant.

"Driving expression" as used herein means promoting the transcription of a nucleic acid.

"Regulating expression" as used herein means influencing the level, time or place of transcription of a nucleic acid. The promoters of the present invention may thus be used to increase, decrease or change in time and/or place transcription of a nucleic acid. For example, they may be used to limit the transcription to certain cell types, tissues or organs, or during a certain period of time, or in response to certain environmental conditions.

The term "plant expressible" means being capable of regulating expression in a plant, plant cell, plant tissue and/or plant organ.

A "fragment" as used herein means a portion of a nucleic acid sequence. Suitable fragments useful in the methods of the present invention are functional fragments, which retain at least one of the functional parts of the promoter and hence are still capable of driving and/or regulating expression. Examples of functional fragments of a promoter include the minimal promoter, the upstream regulatory elements, or any combination thereof.

"Inducible promoters" are responsive to environmental stimuli and provide precise regulation of transgene expression through external control. Inducible promoters are useful for the regulation of potentially stress-related genes that are activated as a result of biotic and abiotic stresses. The differential expression during environmental stimuli helps in meaningful resource utilization.

The term "stress inducible" shall be taken to indicate that expression is predominantly in a stress such as water, heat or salinity. Expression may be driven and/or regulated in the seed, embryo, scutellum, aleurone, endosperm, leaves, flower, calli, meristem, shoot meristem, discriminating centre, shoot, shoot meristem and root.

The term "constitutive" means having no or very few spatial or temporal regulations. The term "constitutive expression" as used herein refers to a substantially continuously expression in substantially all tissues of the organism. The skilled craftsman will understand that a "constitutive promoter" is a promoter that is active during most, but not necessarily all, phases of growth and development of the organism and throughout most, but not necessarily all, parts of an organism.

The term "genetic construct" as used herein means a nucleic acid made by genetic engineering.

The term "operably linked" to a promoter as used herein means that the transcription is driven and/or regulated by that promoter. A person skilled in the art will understand that being operably linked to a promoter preferably means that the promoter is postponed upstream (i.e. at the 5-end) of the operably linked nucleic add. The distance to the operably linked nucleic acid may be variable, as long as the promoter of the present invention is capable of driving and/or regulating the transcription of the operably linked nucleic acid. For example, between the promoter and the operably linked nucleic acid, there might be a cloning site, an adaptor, a transcription or translation enhancer.

The operably linked nucleic acid may be any coding or non-coding nucleic acid. The operably linked nucleic acid may be in the sense or in the anti-sense direction. Typically in the case of genetic engineering of host cells, the operably linked nucleic acid is to be introduced into the host cell and is intended to change the phenotype of the host cell. Alternatively, the operably linked nucleic acid is an endogenous nucleic acid from the host cell.

The term "transcription terminator" as used in herein refers to a DNA sequence at the end of a transcriptional unit which signals termination of transcription. Terminators are 3-non-translated DNA sequences usually containing a polyadenylation signal, which facilitates the addition of polyadenylate sequences to the 3-end of a primary transcript. Terminators active in and/or isolated from viruses, yeasts, molds, bacteria, insects, birds, mammals and plants are known and have been described in literature. Examples of terminators suitable for use in the genetic constructs of the present invention include the *Agrobacterium tumefaciens* nopaline synthase (NOS) gene terminator, the *Agrobacte-*

*rium tumefaciens* octopine synthase (OCS) gene terminator sequence, the Cauliflower mosaic virus (CaMV) 35S gene terminator sequence, the *Oryza sativa* ADP-glucose pyrophosphorylase terminator sequence (t3 Bt2), the *Zea mays* zein gene terminator sequence, the rbcs-1A gene terminator, and the rbcs-3A gene terminator sequences, amongst others.

An "expression cassette" as meant herein refers to a minimal genetic construct necessary for expression of a nucleic acid. A typical expression cassette comprises a promoter-gene-terminator combination. An expression cassette may additionally comprise cloning sites, for example Gateway recombination sites or restriction enzyme recognition sites, to allow easy cloning of the operably linked nucleic acid or to allow the easy transfer of the expression cassette into a vector. An expression cassette may further comprise 5' untranslated regions, 3' untranslated regions, a selectable marker, transcription enhancers or translation enhancers.

The "transformation vector" is a genetic construct, which may be introduced in an organism by transformation and may be stably maintained in said organism. Some vectors may be maintained in for example *Escherichia coli, A. tumefaciens, Saccharomyces cerevisiae* or *Schizosaccharomyces pombe*, while others such as phagemids and cosmid vectors, may be maintained in bacteria and/or viruses. Transformation vectors may be multiplied in their host cell and may be isolated again therefrom to be transformed into another host cell. Vector sequences generally comprise a set of unique sites recognized by restriction enzymes, the multiple cloning sites (MCS), wherein one or more non-vector sequence(s) can be inserted. Vector sequences may further comprise an origin of replication which is required for maintenance and/or replication in a specific host cell. Examples of origins of replication include, but are not limited to, the f1-ori and colE1.

"Expression vector" form a subset of transformation vectors, which, by virtue of having the appropriate regulatory sequences, enable expression of the inserted non-vector sequence(s). Expression vectors have been described which are suitable for expression in bacteria for example *E. coli*; fungi for example *S. cerevisiae, S. pombe, Pichia pastoris* or the like; insect cells for example baculoviral expression vectors; animal cells for example COS or CHO cells and plant cells. One suitable expression vector according to the present invention is a plant expression vector, useful for the transformation of plant cells, the stable integration in the plant genome, the maintenance in the plant cell and the expression of the non-vector sequences in the plant cell.

The term "selectable marker" includes any gene, which confers a phenotype to a cell in which it is expressed, to facilitate the identification and/or selection of cells that are transfected or transformed. Suitable markers may be selected from markers that confer antibiotic or herbicide resistance. Cells containing the genetic construct will thus survive antibiotics or herbicide concentrations that kill untransformed cells. Examples of selectable marker genes include genes conferring resistance to antibiotics for example nptll encoding neomycin phosphotransferase capable of phosphorylating neomycin and kanamycin, or hpt encoding hygromycin phosphotransferase capable of phosphorylating hygromycin; or herbicides for example bar which provides resistance to Basta; aroA or gox providing resistance against glyphosate; or genes that provide a metabolic trait for example manA that allows plants to use mannose as sole carbon source. Visual marker genes result in the formation of colour for example beta-glucurodinase, (GUS); luminescence for example luciferase or fluorescence for example Green Fluorescent Protein (GFP) and derivatives thereof. Further examples of suitable selectable marker genes include the ampicillin resistance (Ampr), tetracycline resistance gene (Tcr), bacterial kanamycin resistance gene (Kanr), phosphinothricin resistance gene, and the chloramphenicol acetyltransferase (CAT) gene, amongst others.

The term "transformation" as used herein encompasses the transfer of an exogenous nucleic acid into a host cell, irrespective of the method used for transfer. In particular for plants, tissues capable of clonal propagation, whether by organogenesis or embryogenesis, are suitable to be transformed with a genetic construct of the present invention and a whole plant may be regenerated therefrom. The particular tissue chosen will vary depending on the clonal propagation systems available for, and best suited to, the particular plant species being transformed. Exemplary tissue targets include leaf disks, pollen, embryos, cotyledons, hypocotyls, megagametophytes, callus tissue, existing meristematic tissue (for example apical meristem, axillary buds, or root meristems), and induced meristem tissue (for example cotyledon meristem and hypocotyl meristem). The nucleic acid may be transiently or stably introduced into a plant cell and may be maintained non-integrated, for example, as a plasmid. Alternatively, it may be integrated into the plant genome.

The term "plant" or "plants" as used herein encompasses whole plants, ancestors and progeny of plants and plant parts, including seeds, shoots, stems, roots (including tubers), and plant cells, tissues and organs. The term "plant" therefore also encompasses suspension cultures, embryos, meristematic regions, callus tissue, gametophytes, sporophytes, pollen, and microspores.

The present invention provides nucleic acid sequences useful for driving and/or regulating expression of an operably linked nucleic acid in plants. The present invention provides isolating and deriving these nucleic acid sequences from monocot plants for example rice, as well as employing them in driving and/or regulating expression of an operably linked nucleic acid. The present invention therefore concerns promoters, genetic constructs, expression cassettes, transformation vectors, expression vectors, host cells and transgenic plants having the nucleic acids according to the present invention. The present invention also concerns methods for driving and/or regulating expression of a nucleic acid and methods for the production of transgenic plants.

The isolated nucleic acid sequences having nucleic acids as presented in SEQ ID NO 1 to 10, preferably SEQ ID NO 3 or SEQ ID NO 6 or SEQ ID NO 7 or SEQ ID NO 9 were isolated from *Oryza sativa* and have been found to be capable of driving and regulating expression of an operably linked nucleic acid; their expression patterns have also been characterized. Therefore, the present invention offers a collection of hitherto unknown isolated nucleic acids, which isolated nucleic acids are useful as promoters.

Accordingly, the present invention provides isolated nucleic acid sequences capable of driving and/or regulating expression, having:

(a) a nucleic acid having sequence as set forth in any one of SEQ ID NO 1 to 10 or the complement of any one of SEQ ID NO 1 to 10; preferably SEQ ID NO 3 or SEQ ID NO 6 or SEQ ID NO 7 or SEQ ID NO 9 or the complement thereof; or (b) a nucleic acid having at least 90% sequence identity in a continuous stretch with any of the nucleic acid sequence as set forth in any one of SEQ ID NO 1 to 10; preferably SEQ ID NO 3 or SEQ ID NO 6 or SEQ ID NO 7 or SEQ ID NO 9 or the complement thereof, or (c) a nucleic acid sequence which hybridizes with any of the nucleic acid sequence as set forth in any one of SEQ ID NO 1 to 10; preferably SEQ ID NO 3 or SEQ ID NO 6 or SEQ ID NO 7 or SEQ ID NO 9 or the complement thereof. The hybridization can be carried out under stringent conditions such as at annealing temperatures of about 60° C. to about 68° C.

The present invention is not limited to the nucleic acids as presented by SEQ ID NO 1 to 10. A person skilled in the art will recognize that variants or fragments of a nucleic add may occur, whilst maintaining the same functionality. These variants or fragments may be manmade (e.g. by genetic engineering) or may even occur in nature. Therefore, the present invention extends to variant nucleic acids and fragments of any of SEQ ID NO 1 to 10, which variants or fragments are useful in the methods of the present invention. Such variants and fragments include:

(a) a nucleic acid as given in any one of SEQ ID NO 1 to 10 or the complement of any one of SEQ ID NO 1 to 10; or (b) a nucleic acid having at least 90% sequence identity in a continuous stretch with any of the DNA sequences as given in any one of SEQ ID NO 1 to 10; or (c) a nucleic acid specifically hybridizing with any of the DNA sequences as given in any one of SEQ ID NO 1 to 10; or (d) a fragment of any of the nucleic acids as defined in (a) to (c), which fragment is capable of driving and/or regulating expression.

Suitable variants of any one of SEQ ID NO 1 to 10 encompass homologues which have in increasing order of preference at least 90%, 91%, 92%, 93%, 94%, 95%, 96%, 97%, 98% or 99% sequence identity with any one of the nucleic acids as represented in SEQ ID NO 1 to 10.

The percentage of identity may be calculated using an alignment program. Preferable, a pair-wise global alignment program may be used. This algorithm maximizes the number of matches and minimizes the number of gaps.

Search and identification of homologous nucleic acids, would be well within the realm of a person skilled in the art. Such methods involve screening sequence databases with the sequence provided by the present invention, for example any one of SEQ ID NO 1 to 10. Useful sequence databases include but are not limited to Genbank the European Molecular Biology Laboratory Nucleic acid Database (EMBL) or versions thereof, or the MIPS database. Different search algorithms and software for the alignment and comparison of sequences are well known in the art. Such software includes, for example GAP, BSETFIT, BLAST, FASTA and TFASTA. Preferably BLAST software is used, which calculates percent sequence identity and performs a statistical analysis of the similarity between the sequences. The suite of programs referred to as BLAST programs has 5 different implementations: three designed for nucleotide sequence queries (BLASTN, BLASTX and TBLASTX) and two designed for protein sequence queries (BLASTP and TBLASTN). The software for performing BLAST analysis is publicly available through the National Centre for Biotechnology Information.

The sequences of the genome of *Arabidopsis thaliana* and the genome of *Oryza sativa* are now available in public databases such as Genbank. Other genomes are currently being sequenced. Therefore, it is expected that as more sequences of the genomes of other plants become available, homologous promoters may be identifiable by sequence alignment with any one of SEQ ID NO 1 to SEQ ID NO 8.

The skilled person will readily be able to find homologous promoters from other plant species, for example from other crop plants, such as maize. Homologous promoters from other crop plants are especially useful for practicing the methods of the present invention in crop plants.

One example of homologues having at least 90% sequence identity in a continuous stretch with any one of SEQ ID NO 1 to 10 are allelic variants of any one of SEQ ID NO 1 to 10. Allelic variants are variants of the same gene occurring in two different individuals of the same species and usually allelic variants differ by slight sequence changes. Allelic variants may encompass Single Nucleotide Polymorphisms (SNPs) as well as Small Insertion/Deletion Polymorphisms (INDELs). The size of INDELs is usually less than 100 bp. SNPs and INDELs form the largest set of sequence variants in naturally occurring polymorphic strains of most organisms.

Homologues suitable for use in the methods according to the invention may readily be isolated from their source organism via the technique of PCR or hybridization. Their capability of driving and/or regulating expression may readily be determined, for example, by following the methods described in the examples section by simply substituting the sequence used in the actual example with the homologue.

Also encompassed within the present invention are promoters, having a fragment of any of the nucleic acids as presented by any one of SEQ ID NO 1 to 10 or variants or compliments thereof as described hereinabove.

Suitable fragments may range from at least about 20 base pairs or about 50, 100, 150, 200, 250, 300, 350, 400, 450, 500, 550, 600, 650, 700, 750, 800, 850, 900, 950 or 1000 base pairs, up to about the full length sequence of the invention. These base pairs are typically immediately upstream of the transcription initiation start, but alternatively may be from anywhere in the promoter sequence.

Suitable fragments useful in the methods of the present invention may be tested for their capability of driving and/or regulating expression by standard techniques well known to the skilled person or by the following method described in the Example section.

The promoters as disclosed in any one of SEQ ID NO 1 to 10, preferably SEQ ID NO 3 or SEQ ID NO 6 or SEQ ID NO 7 or SEQ ID NO 9 or the complement thereof are isolated as nucleic acids of approximately 2 kb from the upstream region of particular rice coding sequences (CDS). Generally, a promoter may comprises from coding sequence to the upstream direction: (i) an 5 UTR of pre-messenger RNA, (ii) a minimal promoter having the transcription initiation element (Inr) and more upstream a TATA box, and (iii) may contain regulatory elements that determine the specific expression pattern of the promoter.

The promoter is preferably a plant-expressible promoter.

The expression pattern of the promoters according to the present invention was studied in detail and it was found that many of them were stress inducible. The stress can be induced by abiotic stress factors or biotic stress. Typically, abiotic stress can be induced by environmental factors such as water, temperature variation such as heat stress or cold stress, salinity and the like. Biotic stress can be induced by an infection of a bacterium, virus or fungi such as *Fusarium* species known to a person skilled in the art. The invention also provides for abiotic stress induced by a biotic stress i.e. an infection caused by an organism.

The inventors surprisingly found that the nucleic acid SEQ ID NO 1 can be expressed under heat and cold stress. SEQ ID NO2, SEQ ID NO 4, and/or SEQ ID NO 8 can be expressed under salt, water, heat and cold stress. SEQ ID NO 5 and/or SEQ ID NO 6 can be expressed under water, heat and cold stress. SEQ ID NO 3 and/or SEQ ID NO 9 can be expressed under water and salt stress and SEQ ID NO 7 can be expressed under water and cold stress. The nucleic acid SEQ ID NO 6 expressed under salt, water, heat and cold stress; SEQ ID NO 3 and/or SEQ ID NO 9 expressed under water and salt stress; and SEQ ID NO 7 expressed under salt, water and cold stress is preferred. Accordingly, the present invention provides "stress inducible" promoters.

Alternatively and/or additionally, some promoters of the present invention display a constitutive expression pattern. For example, SEQ ID NO 1 showed strong expression in leaf tissue as well as weak expression in roots, flowers and young spikelet. Further, SEQ ID NO 1 showed expression after heat and cold stress. Accordingly, the present invention provides a promoter as described hereinabove, which can be a constitutive promoter.

The "expression pattern" of a promoter is not only influenced by the spatial and temporal aspects, but also by the level of expression. The level of expression is determined by the so-called "strength" of a promoter. Depending on the resulting expression level, a distinction is made herein between "weak" or "strong" promoters.

The present invention also provides an expression cassette, a vector which may be a transformation vector or a plant expression vector having a genetic construct as described above.

Typically, a plant expression vector according to the present invention comprises a nucleic acid of any one of SEQ ID NO 1 to 10, preferably SEQ ID NO 3 or SEQ ID NO 6 or SEQ ID NO 7 or SEQ ID NO 9 or a variant thereof as described hereinabove, optionally operably linked to a second nucleic acid. Typically, a plant expressible vector according to the present invention further comprises T-DNA regions for stable integration into the plant genome (for example the left border and the right border regions of the Ti plasmid). FIG. 1A shows a map of the vector having the promoter of the present invention cloned in pMDC 164.

The genetic constructs of the invention may further comprise a "selectable marker". Furthermore, the present invention encompasses a host cell having a promoter, or a genetic construct, or an expression cassette, or a transformation vector or an expression vector according to the invention as described hereinabove. In particular embodiments of the invention, the host cell is selected from bacteria, algae, fungi, yeast, plants host cells.

In one particular embodiment, the invention provides a transgenic plant cell having a promoter according to the invention, or a nucleic acid, or a genetic construct, or an expression cassette, or a transformation vector or an expression vector according to the invention as described hereinabove. Preferably said plant cell is a dicot plant cell or a monocot plant cell more preferably a cell of any of the plants as mentioned herein. The dicot plant cell according to the present invention can be cotton, chilli, cauliflower, tomato, or brinjal. The monocot plant cell according to the present invention can be rice, wheat, corn, sorghum, or pearl millet. Preferably, in the transgenic plant cell according to the invention, the promoter or the genetic construct of the invention is stably integrated into the genome of the plant cell.

The invention also provides a method for the production of a transgenic plant, having (a) introducing into a plant cell a promoter, for example any one of SEQ ID NO 1 to SEQ ID NO 10, preferably SEQ ID NO 3 or SEQ ID NO 6 or SEQ ID NO 7 or SEQ ID NO 9 or variant or fragment thereof, or a genetic construct, or an expression cassette, or a transformation vector or an expression vector according to the present invention and as described hereinabove, and (b) optionally cultivating said plant cell under conditions promoting plant growth.

Introducing the promoter (isolated nucleic acid sequence) of the present invention, or genetic construct or expression cassette, or transformation vector or expression vector, into a host cell (e.g. plant cell) is preferably achieved by transformation.

Transformation of a plant species is now a fairly routine technique. Advantageously, any of several transformation methods may be used to introduce the nucleic acid of the invention into a suitable ancestor cell. Transformation methods include the use of liposomes, electroporation, chemicals that increase free DNA uptake, injection of the DNA directly into the plant, particle gun bombardment, and transformation using viruses or pollen and microprojection. Methods may be selected from the calcium/polyethylene glycol method for protoplasts; electroporation of protoplasts; microinjection into plant material; DNA or RNA-coated particle bombardment infection with (non-integrative) viruses and the like. A preferred transformation method for the production of transgenic plant cells according to the present invention is an *Agrobacterium* mediated transformation method.

In some embodiments provided are transgenic rice plants having any one of the promoters of the present invention preferably produced via *Agrobacterium* mediated transformation using any of the well-known methods for rice transformation.

Generally after transformation, plant cells or cell groupings are selected for the presence of one or more markers which are encoded by plant-expressible genes co-transferred with the gene of interest (which could be under the control of any of the promoters of the present invention), following which the transformed material may be cultivated under conditions promoting plant growth.

The resulting transformed plant cell may then be used to regenerate a transformed plant in a manner known to persons skilled in the art. Accordingly, the method for the production of a transgenic plant as described hereinabove, may further comprise regenerating a plant from the plant cell in which the promoter or fragments thereof is introduced.

The present invention further provides a plant having a plant cell as described hereinabove. The plants may also be able to grow, or even reach maturity including for example fruit production, seed formation, seed ripening and seed setting.

Furthermore, progeny may be produced from these seeds, which progeny may be fertile. Alternatively or additionally, the transformed and regenerated plants may also produce progeny by non-sexual propagation such as cloning, grafting. The generated transformed plants may be propagated by a variety of means, such as by clonal propagation or classical breeding techniques. For example, a first generation (or T1) transformed plant may be selfed to give homozygous second generation (or T2) transformants, and the T2 plants further propagated through classical breeding techniques.

The generated transformed organisms may take a variety of forms. For example, they may be chimeras of transformed cells and non-transformed cells; clonal transformants (for example all cells transformed to contain the expression cassette); grafts of transformed and untransformed tissues (for example in plants, a transformed rootstock grafted to an untransformed scion).

Following DNA transfer and growth of the transformed cells, putatively transformed plant cells or plants may be evaluated, for instance using Southern analysis, for the presence of the gene of interest, copy number and/or genomic organization. Alternatively or additionally, expression levels or expression patterns of the newly introduced DNA may be undertaken using northern and/or Western analysis, both techniques being well known to persons having ordinary skill in the art.

The present invention clearly extends to plants obtainable by any of the methods according to the present invention, which plants comprise any of the isolated promoters or the constructs of the present invention. The present invention clearly extends to any plant parts and propagules of such plant. The present invention extends further to encompass the progeny of a primary transformed cell, tissue, organ or whole plant that has been produced by any of the aforementioned methods, the only requirement being that progeny exhibit the same genotypic and/or phenotypic characteristic(s) as those produced in the parent by the methods according to the invention. The invention also extends to harvestable parts of a plant, such as but not limited to seeds, leaves, fruits, flowers, stem cultures, stem, rhizomes, roots, tubers, bulbs and cotton fibers.

The present invention provides a method for regulating stress in plants including transforming a plant cell with a nucleic acid sequence of interest operably linked to a promoter of the present invention, or transforming the plant or plant cell with an expression cassette or a transformation vector or an expression vector having the genetic construct of the invention and contacting the plant or plant cell with a substance or organism that induces the expression of the promoter.

The invention further provides a method for driving and/or regulating expression of a nucleic acid in a plant or plant cell, having:
  a) subjecting a transgenic plant having the genetic construct having nucleic acid sequence of isolated nucleic acid of the present invention operably linked to a GUS gene to a stress condition such as water stress, heat stress, cold stress and/or salinity stress; and
  b) investigating the expression of said nucleic acid sequences patterns in the plants by observing the GUS stained plant tissues; and
  c) selecting the plants displaying GUS staining;
where the nucleic acid SEQ ID NO 1 can be expressed under heat and cold stress; SEQ ID NO2, SEQ ID NO 4, and/or SEQ ID NO 8 can be expressed under salt, water, heat and cold stress; SEQ ID NO 5 and/or SEQ ID NO 6 can be expressed under water, heat and cold stress; SEQ ID NO 3 and/or SEQ ID NO 9 can be expressed under water and salt stress and SEQ ID NO 7 can be expressed under water and cold stress. According to an embodiment of the invention, the nucleic acid SEQ ID NO 6 expressed under salt, water, heat and cold stress; SEQ ID NO 3 and/or SEQ ID NO 9 expressed under water and salt stress; and SEQ ID NO 7 expressed under salt, water and cold stress is preferred.

The present invention provides that the stress can be induced by various ways. In one embodiment, according to the present invention, plants can be subjected to water stress by withholding water to the plants for about 1 to 14 days, preferably 5 to 9 days. The stress can be induced by varying the temperature, for example, the plants can be subjected to heat stress by keeping the plants in an incubator at a temperature of about 35° C. to 42° C. for 2 to 8 hours each day for about 2 to 6 days according to an embodiment of the present invention. Preferably, the plants can be subjected to the heat stress by keeping the plants in the incubator at a temperature of about 42° C. for about 8 hours each day for about 2 to 6 days. Similarly, subjecting the plants to cold stress can be by keeping them in an incubator at a temperature to 4° C. to 8° C. for 2-8 hours. Preferably, the plants can be subjected to cold stress by keeping them in an incubator at a temperature of about 4° C. for about 8 hours each day for about 2 to 6 days. The plants can be subjected to salt stress by irrigating the plants with a solution containing about 100 to 200 Mm NaCl for about 2 to 12 hours in an embodiment of the present invention. Preferably, the plants can be subjected to salt stress by irrigating the plants with a solution containing about 150 mM NaCl for about 3 to 12 hours. The present invention also includes abiotic stress induced by a biotic factor such as an infection by organisms such as bacteria, virus, fungi such as *Fusarium*.

The observation of the expression patterns of the isolated nucleic acid sequences, i.e. the promoters of the present invention can be made by visual inspection of the GUS stained tissues such as roots tissues, leaves, or flower parts (such as anthers). Preferably, sampling can be done once before the start of subjecting the plants to a stress test and once after the stress test. A person skilled in the art would understand that the expression of some promoters may be weak in certain tissues and may only be visible with very sensitive detection methods. GUS staining and GUS quantification protocols are known to a person skilled in the art.

Accordingly, the present invention provides a method as described above, wherein the expression can be a constitutive expression or a stress-inducible expression. For these embodiments, reference is made to the example section where the specific expression patterns of the promoters according to the invention are described and where different types of tissue-specific expression are detailed.

The present invention further encompasses the use of an isolated nucleic acid as defined hereinabove to drive and/or regulate expression of an operably linked nucleic acid.

The person skilled in the art will recognize that provision of sequences SEQ ID NO 1 to 10, readily makes available the tools to isolate related promoters, which may have substantial sequence identity to any of SEQ ID NO 1 to 10.

Example 1

Probe Sets for Highly Upregulated Genes Under Various Stress Condition and Arriving at Promoters A unified gene expression resource like PLEXdb (Plant Expression Database) was used to identify highly up regulated probe sets by comparing different abiotic treatments viz drought, salinity etc. from the selected experiments. By considering each and every combination of every experiment, 8 fold probeset data generated and redundant probesets were deleted. The probesets having higher frequency of occurrence were considered for this study. Predicted mRNA sequence and putative promoter sequences were retrieved from RiceXPro (The Rice Expression Profile Database). The gene IDs and designated promoter name are listed in Table 1.

TABLE 1

Designated promoter name and Gene ID

| Seq. ID. No. | Promoter designation | Gene ID |
| --- | --- | --- |
| 1 | RP2H | Os08t0442900-01 |
| 2 | RP9H | Os11t0181200-01 |

TABLE 1-continued

Designated promoter name and Gene ID

| Seq. ID. No. | Promoter designation | Gene ID |
|---|---|---|
| 3 | RP10H | Os08t0286500-01 |
| 4 | RP4 | Os05t0542500-01 |
| 5 | RP7 | Os06t0324400-01 |
| 6 | RP8 | Os05t0550600-02 |
| 7 | RP10 | Os03t0245800-02 |
| 8 | RP11 | Os03t0330200-00 |
| 9 | RP3H | Os11t0533400-01 |
| 10 | RP8H | Os03t0133100-01 |

Identification and Isolation of the Promoter Regions of Rice Genes

The promoter regions of these genes were isolated as the DNA region spanning about 2 kb upstream of the translation initiation codon (i.e. first ATG), which codon was excluded. The promoter regions were isolated from genomic DNA of Oryza sativa Indica rice line IR-58025 B developed by International Rice Research Institute (IRRI), Philippines via PCR using specific primers and high fidelity DNA polymerase.

These specific primers comprise CACC site for site directed ligation. These specific primers are herein represented as SEQ ID NO 11 to 30 and are listed in Table 2. Conditions for PCR were as follows: 1 cycle of 3 min at 95° C., 35 cycles of 30 sec at 95° C., 30 sec at 50-60° C. and 2 min at 72° C., and 1 cycle of 7 min at 72° C. [annealing temperature varied for each promoter]. The length of the expected PCR fragment and the annealing temperatures are indicated in Table 3. The corresponding PCR fragment was purified from the PCR reaction mix via gel electrophoresis and subsequent purification with HiYield Gel/PCR DNA Mini kit (Real Genomics).

TABLE 2

Primers of respective promoters

| Seq. ID. No. | Oligo Name | SEQUENCE | Length |
|---|---|---|---|
| 11 | RP2H Forward Primer | CACCGCGGCCGCTCTCTGTGGCTGTTGTGTC | 31 |
| 12 | RP2H Reverse Primer | CTGCAGTGCTCCTCTGCTGTACTG | 24 |
| 13 | RP9H Forward Primer | CACCGCGGCCGCCCATTGCTATCTTCTACCG | 31 |
| 14 | RP8H Reverse Primer | CCATGGCGCTCTCTCTTGCAGTTAAT | 26 |
| 15 | RP10H Forward Primer | CACCGTCGACACTAACTAAGAATCAAATGC | 30 |
| 16 | RP10H Reverse Primer | CCATGGCACGATGATTTCTCCCCTC | 25 |
| 17 | RP4 Forward Primer | CACCGCGGCCGCGGGTTAATGTAGTTCTTGG | 31 |
| 18 | RP4 Reverse Primer | CTGCAGGAATGTTAGAACTCTGATGG | 26 |
| 19 | RP7 Forward Primer | CACCGCGGCCGCGCGATTTGGTCAGCTTCT | 30 |
| 20 | RP7 Reverse Primer | ATTCCATGGCTCTCCCAAGTCCCAACTA | 28 |
| 21 | RP8 Forward Primer | CACCGCGGCCGCGTTTTAGAGTTGGACACAG | 31 |
| 22 | RP8 Reverse Primer | ATTGTCGACCTGAAATTAAGCTGCGAGA | 28 |
| 23 | RP10 Forward Primer | CACCGTCGACTAGTGACTACCAATGCTC | 28 |
| 24 | RP10 Reverse Primer | CCATGGACAGAGTAGAGAGGAAATC | 25 |
| 25 | RP11 Forward Primer | CACCGCGGCCGCTGGATTCATTGGATTGGGC | 31 |
| 26 | RP11 Reverse Primer | ATTGTCGACTTGTTCCTCTTCTCTGGTG | 28 |
| 27 | RP3H Forward Primer | CACCGCGGCCGCGATCACGAATATCAACGCC | 31 |
| 28 | RP3H Reverse Primer | CTGCAGTTTGGAGCGGAGAGAGTT | 24 |
| 29 | RP8H Forward Primer | CACCGCGGCCGCGGTTGCATTACACTGACAG | 31 |
| 30 | RP8H Reverse Primer | CTGCAGTGAGCTGAGTTGAGTGAGT | 25 |

TABLE 3

Annealing temperature and Length of the PCR fragment

| Sr. No. | Promoter designation | Annealing temperature | Length of the PCR fragment |
|---|---|---|---|
| 1 | RP2H | 63 | 1988 |
| 2 | RP9H | 60 | 2133 |
| 3 | RP10H | 63 | 2463 |
| 4 | RP4 | 61 | 2035 |
| 5 | RP7 | 67 | 1949 |
| 6 | RP8 | 67 | 1881 |
| 7 | RP10 | 65 | 2119 |
| 8 | RP11 | 67 | 1977 |
| 9 | RP3H | 60 | 2047 |
| 10 | RP8H | 60 | 2051 |

Example 2

Cloning of Promoter-Gus Reporter Vectors for Plant Transformation

Figure 1B:
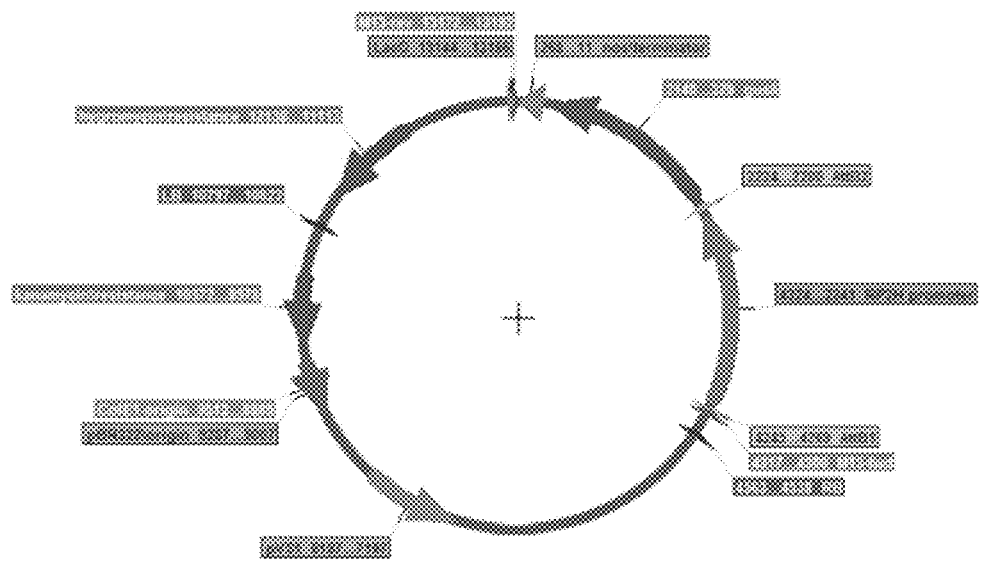
Figure 2:
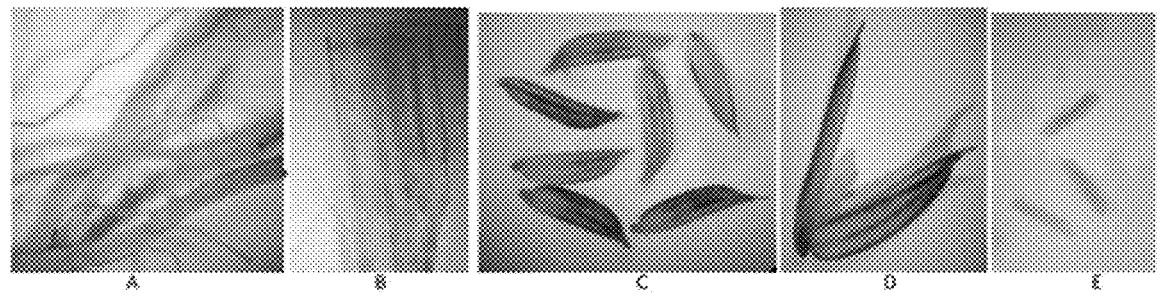
Figure 3:
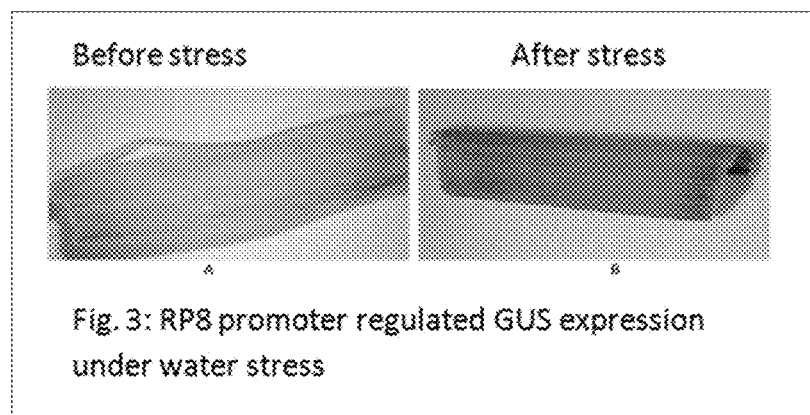
FIGS. 3A-3B is a digital image exhibiting expression pattern of RP8 (SEQ ID NO 6) under water stress. Slight GUS expression was observed in the leaf tissue before stress as can be seen in FIG. 3A and there is a visible increase in GUS expression pattern seen after water stress in FIG. 3B.
Figure 4:
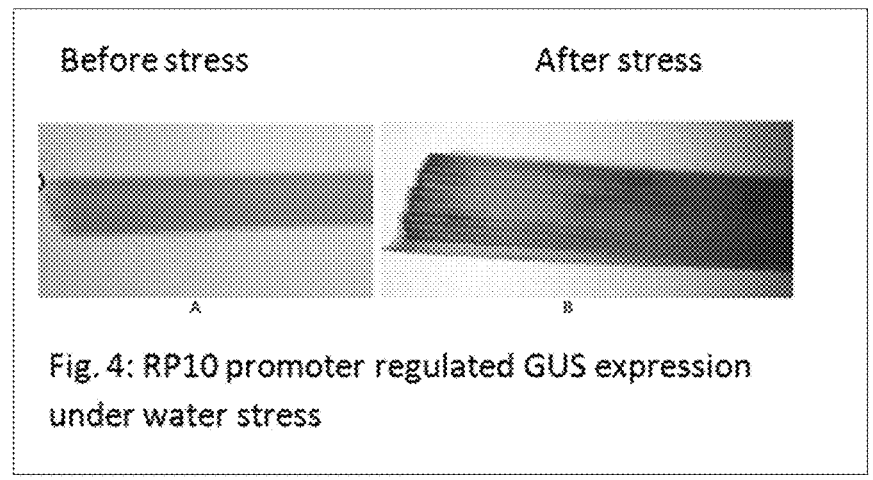
FIG. 4A-4B is a digital image exhibiting expression pattern of RP10 (SEQ ID NO 7) under water stress. No visible GUS expression was observed in the leaf tissue before stress as can be seen in FIG. 4A and there is a visible increase in GUS expression pattern seen after water stress in FIG. 4B.
Figure 5:
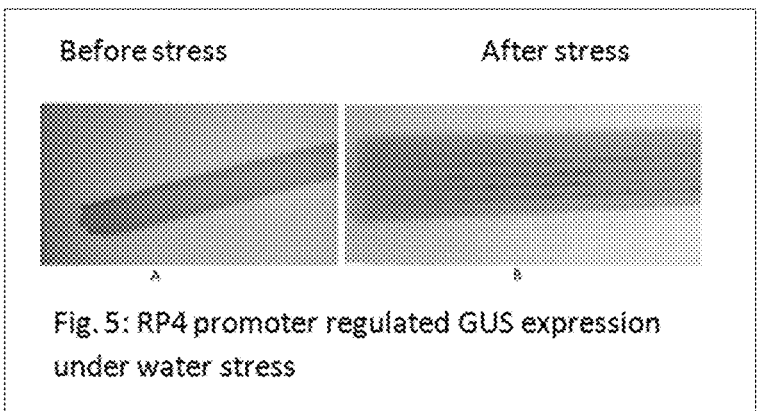
FIGS. 5A-5B is a digital image exhibiting expression pattern of RP4 (SEQ ID NO 4) under water stress. No visible GUS expression was observed in the leaf tissue before stress as can be seen in FIG. 5A and there is a visible increase in GUS expression pattern seen after water stress in FIG. 5B.
Figure 6:
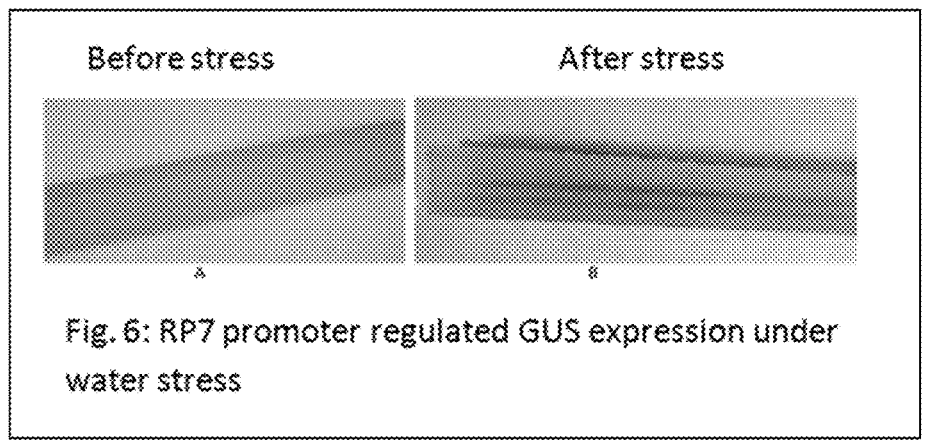
FIGS. 6A-6B is a digital image exhibiting expression pattern of RP7 (SEQ ID NO 5) under water stress. No visible GUS expression was observed in the leaf tissue before stress as can be seen in FIG. 6A and there is a visible increase in GUS expression pattern seen after water stress in FIG. 6B.
Figure 7:
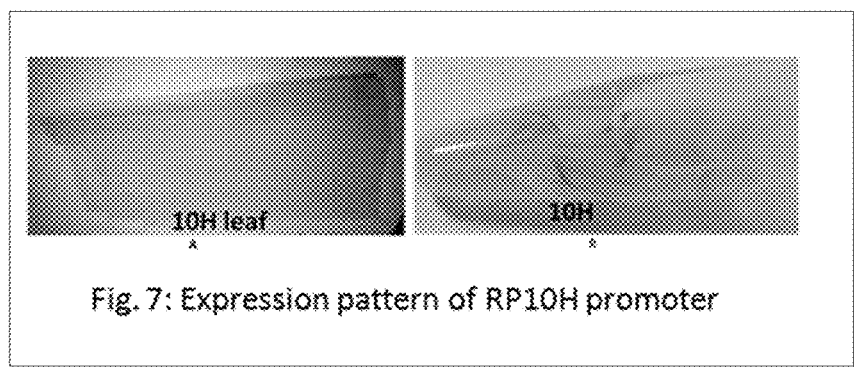
FIGS. 7A-7B is a digital image exhibiting expression pattern of RP10H (SEQ ID NO 3). GUS staining is visible in FIG. 7A leaf tissue and FIG. 7B inflorescence.

The purified PCR fragments of Example 1 corresponding to the promoter regions of the present invention, were cloned into the pENTR™/D-TOPO entry plasmid of the Gateway system (Life Technologies) using the site specific ligation. The identity and base pair composition of the cloned insert was confirmed by sequencing and additionally, the resulting plasmid was tested via restriction digests. In order to clone each of the promoters of the present invention in front of a reporter gene, each entry clone of Example 1 was subsequently used in an "LR recombination reaction" (Gateway) with the destination vector pMDC 164. This destination vector was designed to operably link each promoter of the present invention to the *Escherichia coli* beta-glucuronidase (GUS) gene via the substitution of the Gateway recombination cassette in front of the GUS A gene. Furthermore this destination vector is suitable for transformation of plants and comprises within the T-DNA left and right borders the resulting promoter-GUS cassette and selectable marker and screenable marker cassettes (see FIGS. 1A-1B). The resulting reporter vectors, having a promoter of the present invention operably linked to GUS, are subsequently transformed into *Agrobacterium* strain EHA 105 and subsequently into plants of rice line IR-58025 B developed by International Rice Research Institute (IRRI), Philippines using transformation techniques as mentioned below.

Rice Transformation Protocol

*Agrobacterium*—transformation of rice was performed by method as described in Hiei et al., 2006 with some modification.

Transformation Protocol:

Freshly isolated rice immature embryos from plants grown in a greenhouse (Dawalwadi, Mahyco), after 10-12 days' post anthesis were inoculated with *A. tumefaciens* EHA105 carrying pMDC164 promoter construct.

Three days before infection, *Agrobacterium* strain EHA 105 carrying pMDC164 promoters: GUS were streaked on LB agar with antibiotic selection (Chloramphenicol 10 mg/L and Kanamycin 50 mg/L). and incubated at 28° C.

Just before infection, grown *Agrobacterium* culture scrapped from plate and suspended in (AA) infection medium and ~1.0 OD at 600 nm (stationary phage) used for infection.

Seed sterilization: seeds were de-husked by hand and sterilized in 70% ethanol for 30 seconds and in 1.5% sodium hypochlorite solution for 5 minutes. The immature seeds were rinsed several times in sterile water, and immature embryos of 1.5 mm in length were collected under a stereoscopic dissection microscope.

5 µl of suspended *Agrobacterium*-culture dropped on scutellum of freshly isolated immature embryo incubated for 15 minutes then co-cultivated on (NBA)s medium for 4-6 days in dark at 25° C.

Resting step: After the co-cultivation, elongated shoots were removed from the immature embryos by a scalpel and the immature embryos were cultured on (NBM) medium that contained cefotaxime (250 mg/L) and carbenicillin (100 mg/L) with the scutellum-side up for 5 days Selection step: After resting step immature embryos were transferred on selection medium NBM with cefotaxime (250 mg/L) and hygromycin (50 mg 1/L) for 2 weeks followed by second selection of two weeks on the fresh NBM medium with cefotaxime (250 mg/L) and hygromycin (50 mg 1/L).

Pre-regeneration step: Calluses clearly resistant to hygromycin derived from the scutella were transferred to a pre-regeneration medium (NBPR) that contained hygromycin (40 mg/L) and cefotaxime (250 mg/L) and cultured for 10 days.

Regeneration step: Proliferating calluses with green spots were cultured on an (RNM) regeneration medium that contained hygromycin (30 mg/L) and cefotaxime (250 mg/L).

Rooting: regenerated plantlets were cultured on an (MSN) 1.5 rooting medium that contained hygromycin (30 mg/L).

In all of the following steps, cultures were incubated at 28° C. under 16 hrs. light and 8 hrs. dark.

The plants were hardened to soil in pots and grown to maturity in a greenhouse.

Media Composition:

1] AA-infection: AA salts and amino acids (Toriyama and Hinata, 1985), B5 vitamins, vitamin assay casamino acids (0.5 g/L), sucrose (20 g/L), D-glucose (10 g/L), acetosyringone (0.1 mM), pH 5.2

2] NBM: N6 major salts, B5 minor salts and vitamins, vitamin assay casamino acids (0.5 g/l), L-proline (0.5 g/L), L-glutamine (0.3 g/L), D-maltose (20 g/L), D-mannitol (36 g/L), 2,4-D (2 mg/L), NAA (1 mg/L), BA (0.2 mg/L), Gelrite (5 g/L), pH 5.8

3] NBPR: N6 major salts, B5 minor salts and vitamins, vitamin assay casamino acids (0.5 g/L), L-proline (0.5 g/L), L-glutamine (0.3 g/L), D-maltose (30 g/L), 2,4-D (2 mg/L), 1 NAA (1 mg/L), BA (1 mg/L), Gelrite (7 g/L), pH 5.8

4] RNM: N6 major salts, B5 minor salts and vitamins, vitamin assay casamino acids (0.3 g/L), L-proline (0.3 g/L), L-glutamine (0.3 g/L), D-maltose (30 g/L), NAA (1 mg/L), BA (3 mg/L), agarose Type I (4 g/L), pH 5.8

5] MSN1.5: Full strength of MS major salts, MS minor salts, MS vitamins and myo-inositol (100 mg/L), MS Cacl2, MS iron, (Murashige and Skoog, 1962), sucrose (30 g/L), NAA (1.5 mg/L), phytagel (3 g/L), pH 5.8

Example 3

Expression Patterns of the Promoter-Gus Reporter Cassette in Plants Growth and Harvest of Transgenic Plants or Plant Parts at Various Stages For each promoter-GUS reporter construct T0 transgenic rice plants were generated from transformed cells. Plant growth was performed under normal conditions.

The GUS staining analyses were performed on T0 plants originating from the transformed tissues. The stability of promoter activity in the next generations or progeny plants of the original T0 plant the so-called T1 and T2 plants was evaluated as follows. The T0 plant transformed with the reporter constructs as mentioned in the above paragraphs of Example 2, were grown until maturity of which the seeds (T1 seeds) were harvested and sown to generate progeny T1 plants. These plants were analyzed and the T1 plants were allowed to reach maturity and to set T2 seeds.

The expression pattern of the promoters of the present invention was studied in T0 plants, T1 seeds, T1 plants.

Expression Patterns of the Promoters of the Present Invention Under Different Stress Conditions Rice T1 seeds sown in sandy soil were kept in a culture room with light intensity maintained at 12,000 to 14,000 lux and with a 16-h light/8-h dark cycle at 28° C. After germination, one month old plants were subjected to stress conditions.

Water stress: Water was withheld from transgenic and control plants for 6 days (until almost all the leaves in the pot became completely rolled). Plants were then recovered by providing water for 5 to 9 days. Sampling was done once before the start of water withholding experiment and when the leaves start to roll.

Heat stress: Plants were subjected to heat stress by keeping them in a BOD incubator and adjusting the temperature to 42° C. for 8 hrs. each day for 6 days (until almost all the leaves in the pot became completely rolled).

Salt stress: plants were irrigated with a solution containing 150 mM NaCl for 3 to 12 hrs. for salt stress.

Cold stress: Plants were subjected to cold stress by keeping them in a BOD incubator and adjusting the temperature to 4° C. for 8 hrs. each day for 6 days (until almost all the leaves in the pot became completely rolled).

Sampling was done once before the start of the stress assay and designated as E0 (Initial) and after exposing to stress when the leaves starts to roll and designated as Ef (final).

The following paragraphs describe the observed expression patterns of the promoters of the present invention in more detail. The observations are based on the visual inspection of the GUS stained tissues as described above. It is to be understood that for some promoters expression may be weak and that expression in certain tissues may only be visible with very sensitive detection methods.

Promoter 1

RP2H construct (SEQ ID NO. 1) was investigated. 10 plants of three independent events in T1 generation were analyzed. Strong expression in leaf tissue was observed as well as weak expression in roots, expression was observed in flowers, more particularly in lemma of young spikelet. It was concluded that the promoter is suitable for expression in young tissue, more preferably in young, developing or expanding tissue, more preferably in green tissue. The expression level slightly decreased after water stress and salt stress. There was a slight increase after heat and cold stress. So it was concluded that RP2H behaves like a constitutive promoter which also shows inducibility to temperature variations.

Promoter 2

RP9H construct (SEQ ID NO. 2) was investigated. It was observed that RP9H drives expression of Gus gene, and there was no expression or expression level was very low, therefore not invisible to the naked eye when not exposed to any stress. It was also observed that the promoter can drive expression under various stress conditions. There was significant increase in expression level after water stress. There was 4 fold increase in the expression under salt stress, 28 fold increase under heat stress and cold stress showed 55 fold increase. It is concluded that RP9H is a stress inducible promoter which can increase the expression level of a gene under various stress condition.

Promoter 3

RP10H construct (SEQ ID NO. 3) was investigated. No visible expression was observed in the leaves when the promoter drives Gus gene under no stress condition. RP10H was capable of driving expression in flowers, more particularly in lemma of young spikelet. The expression level increased after exposing to water stress and salt stress. There was a 6 fold increase after water stress in the expression level of Gus gene. After salt stress expression increased to 4 fold after 2 hours and 16 fold after 5 hours. No expression after heat and cold stress was observed. It is concluded that RP10H is water and salt stress inducible promoter.

Promoter 4

RP4 construct (SEQ ID NO. 4) was investigated. Weak expression was observed in the leaves initially. The expression level increased to 16 fold after exposing the plants to water stress, 3 fold increase to salt stress, 0.4 fold increase to heat and 3 fold increase to cold stress after 5 hrs of stress).

Promoter 5

RP7 construct (SEQ ID NO. 5) was investigated. Weak expression was observed in the leaves initially. The expression level increased significantly after exposing the plants to heat stress (2 fold increase). There was a slight increase in the expression under water and cold stress when Gus gene was driven by RP7. Under salt stress the expression increased initially, however decreased after 5 hour of stress.

Promoter 6

RP8 construct (SEQ ID NO. 6) was investigated. Weak expression was observed in the leaves initially. The expression level increased after exposing the plants to water stress (1.4 fold increase). Inducibility to heat (1 fold increase) and cold stress (2 fold increase) was also observed. There was a decrease in expression level after 5 hours of salt stress. It was concluded that RP8 was water stress inducible promoter showing significant inducibility to heat and cold stress as well.

Promoter 7

RP10 construct (SEQ ID NO. 7) was investigated. Weak expression was observed in the leaves initially. The expression level increased to 2.5 fold after exposing the plants to water stress. Inducibility to cold stress was observed with 8 fold increase). There was a very little increase after heat stress and even though there was 1 fold increase after 2 hours of salt stress the inducibility decreased gradually. It was concluded that RP10 was a water and cold stress inducible promoter.

Promoter 8

RP11 construct (SEQ ID NO. 8) was investigated. Weak expression was observed in the leaves initially. The expression level increased to 4.2 fold after exposing the plants to water stress. A steady increase up to 2.8-fold was observed after salt stress after 5 hours). The promoter also showed inducibility to heat and cold stress. After 2 hrs of heat stress there was a 4 fold increase in expression level of Gus which increased to 32 fold after 5 hours. Also a 2 fold increased after 5 hours of cold stress. It was concluded that RP11 was a stress inducible promoter which can increase the expression level of a gene under various stress condition.

Promoter 9

RP3H construct (SEQ ID NO. 9) was investigated. Weak expression was observed in the leaves initially. The expression level significantly increased after exposing the plants to water stress (38 fold increase). There was 4 fold increase in expression level when exposed to 150 mM salt stress for 5 hrs. No significant increase after heat and cold stress was. It was concluded that RP3H is a water and salt stress inducible promoter.

Promoter 10

RP8H construct (SEQ ID NO. 10) was investigated. When RP8H drove the expression of Gus gene, it was observed that there was wither no expression or expression level was very low, therefore not invisible to the naked eye when not exposed to any stress. Also no significant increase in Gus expression was seen when exposed to heat, cold, salt and water stress.

GUS Staining Protocol

The plant material was covered by a Gus solution and incubated up to 16 hours at 37° C. Gus Buffer [phosphate buffer (50 ml), Triton X (0.1% 10 ml), 50 mM Potassium ferricyanate (2 ml), 50 mM Potassium ferrocyanide (2 ml), methanol (20 ml) in distilled water (15 ml) and X-Gluc stock (1 ml of X-Gluc (50 mg) in DMF (1 ml)]. Chlorophyll was extracted by washing with 70% ethanol (for 8 hours).

Gus expression in leaf tissue of T1 plants are shown in FIGS. 2-7, there was slight or no visible GUS expression observed in the tissues of plants before they were exposed to stress as can be seen in (A) images, however there was marked visible increase in GUS expression in tissues of plants after they were exposed to water stress as can be seen in (B) images.

Example 4

GUS Quantification

Quantification of GUS activity was performed by fluorometric assay described in Jefferson et al., 1987 (Jefferson et al., (1987), EMBOJ., 6, 3901-3907) and Gallagher 1992 (Gallagher, S. R. (1992) Academic Press, Inc., New York, pp. 47-59).

Plant extract: 100 mg leaf tissues were ground in 200 μl of extraction buffer [50 mM NaPO4 pH 7.0, 10 mM EDTA, 0.1% Triton X-100, 0.1% sodium lauryl sarcosine, 10 mM β-mercaptoethanol]. The leaf tissue was then centrifuged at 12000 rpm for 15 minutes at 4° C. to remove cell debris. Supernatant was transferred to a fresh tube.

MUG assay: 20 μl homogenates (approximately 5 μg of protein) were mixed with 80 μl of GUS assay buffer [8.8 mg MUG was dissolved in 10 ml (2 mM) extraction buffer. The buffer was freshly prepared just before use]. The mixture was vortexed and incubated at 37° C. for 30 minute and 60 minute in a water bath. Each reaction mixture (2 μl of) and of each MU standard were mixed with stop buffer (475 μl [200 mM Na2CO3 (21.2 gm/L) pH 11.2]). 200 μl of above reaction mixture from above step were loaded by duplicated manner in a micro-titer plate and florescence were determined, excitation at 365 nm and emission at 444 nm.

picoMole MU/μg of protein/minute =

$$\frac{\text{picoMole Mu/well}}{\text{amount of protein in 10 μl} \times \text{minute of assay}}$$

Concentrated MU calibration stock solution: Mix 9.9 mg in 50 ml D/W to prepare 1 mM MU stock. Make 1:10 dilution to get 100 μM MU stock and 1:50 dilution to get 20 μM stock solution. For standard curve used 0, 4, 8, 12, 20, 40, 100, 250, 500 pmol MU.

Gus quantification data is presented in Table 4 and 5.

TABLE 4

Gus Quantification data

Salt stress (150 mM) pmole MU/mg protein/min

| Sample | 0 hr | 2 hr | 5 hr |
|---|---|---|---|
| Control | 18.06 | 20.62 | 5.58 |
| RP2H | 212.30 | 116.90 | 116.90 |
| RP3H | 21.70 | 122.30 | 125.30 |
| RP8H | 0 | 0 | 0 |
| RP9H | 1.10 | 6.47 | 90.80 |
| RP10H | 4.74 | 26.29 | 83.40 |
| RP4 | 45.23 | 54.82 | 195.00 |
| RP7 | 229.41 | 254.31 | 193.02 |
| RP10 | 118.06 | 263.41 | 47.23 |
| RP11 | 45.05 | 89.15 | 171.79 |

TABLE 5

Gus Quantification data

Salt stress (150 mM) pmole MU/mg protein/min

| Sample | 0 hr | 2 hr | 5 hr |
|---|---|---|---|
| Control | 18.05958754 | 20.61898005 | 5.582652 |
| RP8 | 1987.289516 | 1672.672257 | 2792.164 |

TABLE 6

Gus Quantification data-Table 6 represents significant increase in the Gus 5 expression pattern of RP9H, RP4, RP7, RP8, RP2H and RP11 after heat stress Heat stress pmole MU/mg protein/min

| Sample | 0 hr | 2 hr | 5 hr |
|---|---|---|---|
| Control | 4.07 | 3.46 | 3.77 |
| RP9H | 5.98 | 0.00 | 176.26 |
| RP4 | 105.28 | 34.95 | 152.48 |
| RP7 | 35.83 | 52.18 | 107.73 |
| RP8 | 16.28 | 32.28 | 34.58 |
| RP10 | 8.62 | 11.83 | 10.62 |

TABLE 7

Gus Quantification data-Table 7 represents significant increase in the Gus expression pattern of RP9H, RP4, RP7, RP8, RP2H and RP11 after heat stress Heat stress pmole MU/mg protein/min

| Sample | 0 hr | 2 hr | 5 hr |
|---|---|---|---|
| Control | 4.07 | 3.46 | 3.77 |
| RP2H | 818.23 | 671.34 | 1334.39 |
| RP11 | 8.98 | 48.97 | 296.38 |

TABLE 8

Gus Quantification data-Table 8 represents the Gus expression pattern of RP2H, RP3H, RP8H, RP9H, RP10H, RP4, RP7, RP8, RP10 and RP11 to 2 hours and 5 hours of cold stress.

| | Cold stress pmole MU/mg protein/min | | |
|---|---|---|---|
| Sample | 0 hr | 2 hr | 5 hr |
| Control | 0 | 0 | 0 |
| RP3H | 40.48 | 30.40 | 0.00 |
| RP9H | 0 | 1.63 | 55.03 |
| RP10H | 1.243524255 | 2.096052367 | 2.429907 |
| RP4 | 55.84 | 170.33 | 278.07 |
| RP7 | 173.54 | 182.46 | 231.65 |
| RP11 | 9.27 | 15.18 | 27.94 |

TABLE 9

Gus Quantification data-Table 9 represents the Gus expression pattern of RP2H, RP3H, RP8H, RP9H, RP10H, RP4, RP7, RP8, RP10 and RP11 to 2 hours and 5 hours of cold stress.

| | Cold stress pmole MU/mg protein/min | | |
|---|---|---|---|
| Sample | 0 hr | 2 hr | 5 hr |
| Control | 0 | 0 | 0 |
| RP2H | 1138.486529 | 1223.994169 | 2295.215 |
| RP8 | 310.3441585 | 290.9299799 | 981.2915 |
| RP10 | 46.52182127 | 94.33485234 | 436.2004 |

TABLE 10

Gus Quantification data-Table 10 represents the significant increase in the Gus expression pattern of RP10, RP8, RP4, RP10H, RP11 after water stress.

| | Water Stress pmole MU/mg protein/min | |
|---|---|---|
| Sample | Before Stress | After Stress |
| 25B (ve) | 1.886 | 12.995 |
| 10-1A | 60.663 | 212.883 |
| 8-2B | 333.293 | 801.69 |
| 4-1A | 101.512 | 1787.8 |
| 10H-4B | 31.26 | 242.7 |
| 11-8A | 37.726 | 199.423 |

TABLE 11

Gus Quantification data-Table 11 represents the significant increase in the Gus expression pattern of RP2H, RP3H, RP9H, RP10H, RP7 after water stress.

| | Water Stress pmole MU/mg protein/min | |
|---|---|---|
| Sample | Before Stress | After Stress |
| Control | 1.886 | 12.995 |
| RP2H | 1241.50 | 935.49 |
| RP3H | 3.40 | 134.55 |
| RP9H | 0 | 438.37 |

TABLE 11-continued

Gus Quantification data-Table 11 represents the significant increase in the Gus expression pattern of RP2H, RP3H, RP9H, RP10H, RP7 after water stress.

| | Water Stress pmole MU/mg protein/min | |
|---|---|---|
| Sample | Before Stress | After Stress |
| RP10H | 31.26 | 242.7 |
| RP7 | 1457.35 | 2644.40 |

Observations/Inferences of the Above Tables

Figure 8:
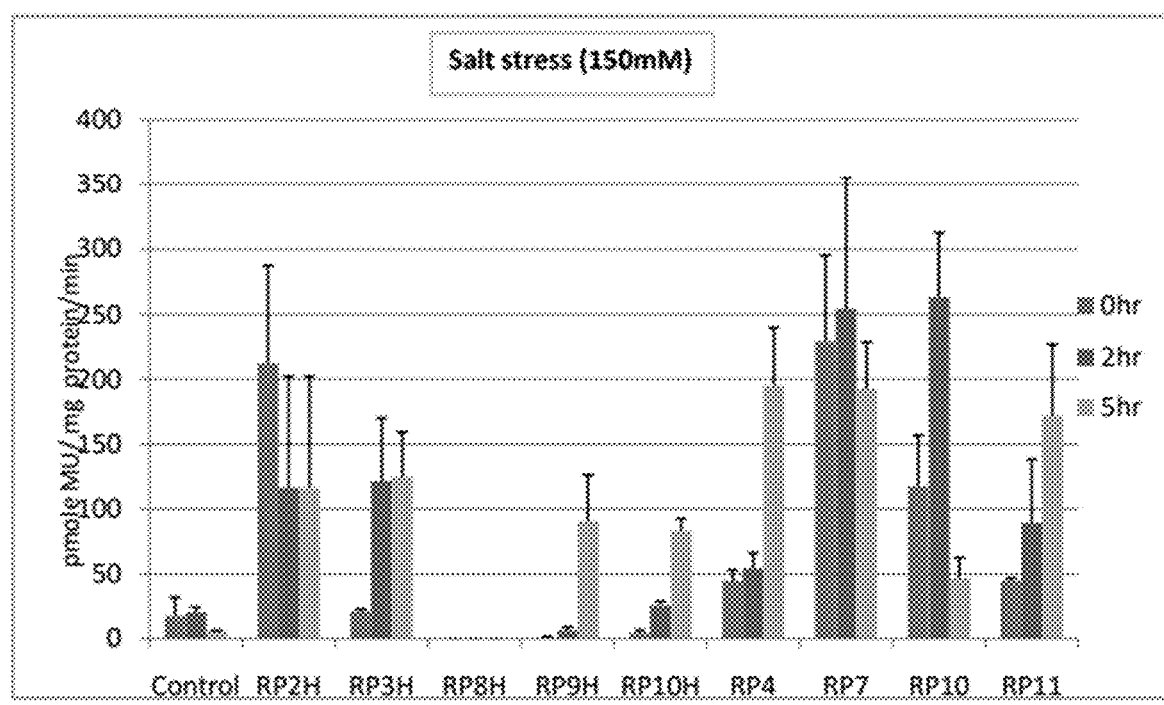
FIG. 8 is a graph of Fluorometric analysis of Gus expression in leaf tissues of different promoters viz RP2H, RP3H, RP8H, RP9H, RP10H, RP4, RP7, RP10, RP11 after salt stress assay along with control.
Figure 9:
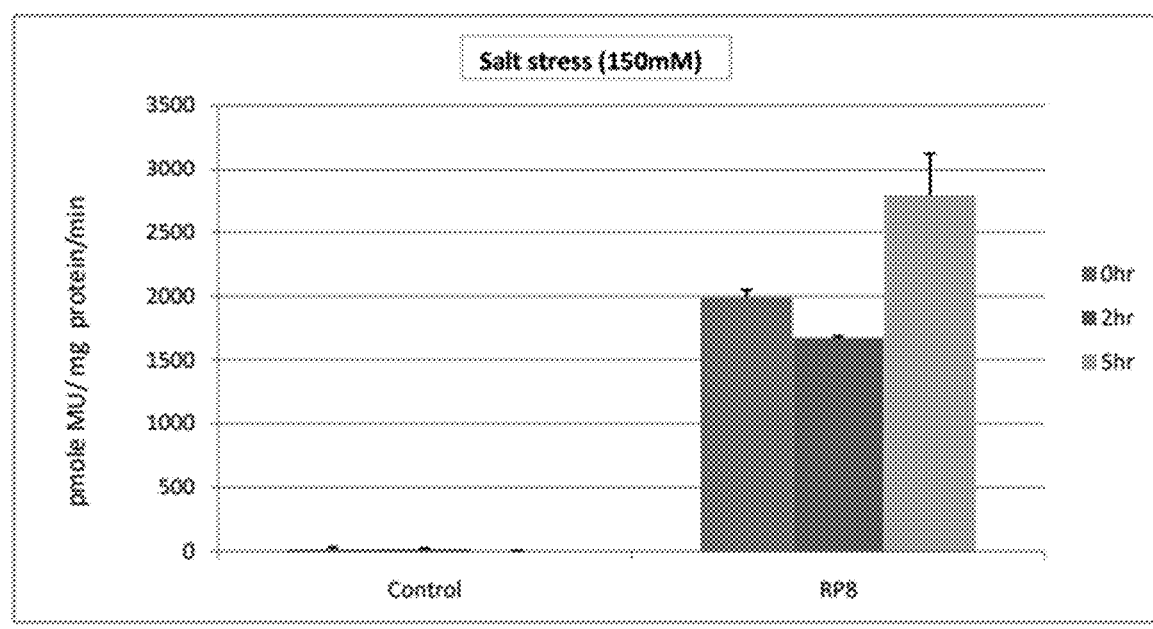
FIG. 9 is a graph of Fluorometric analysis of Gus expression in leaf tissues of different promoters viz RP8 along with control after salt stress assay.
Figure 10:
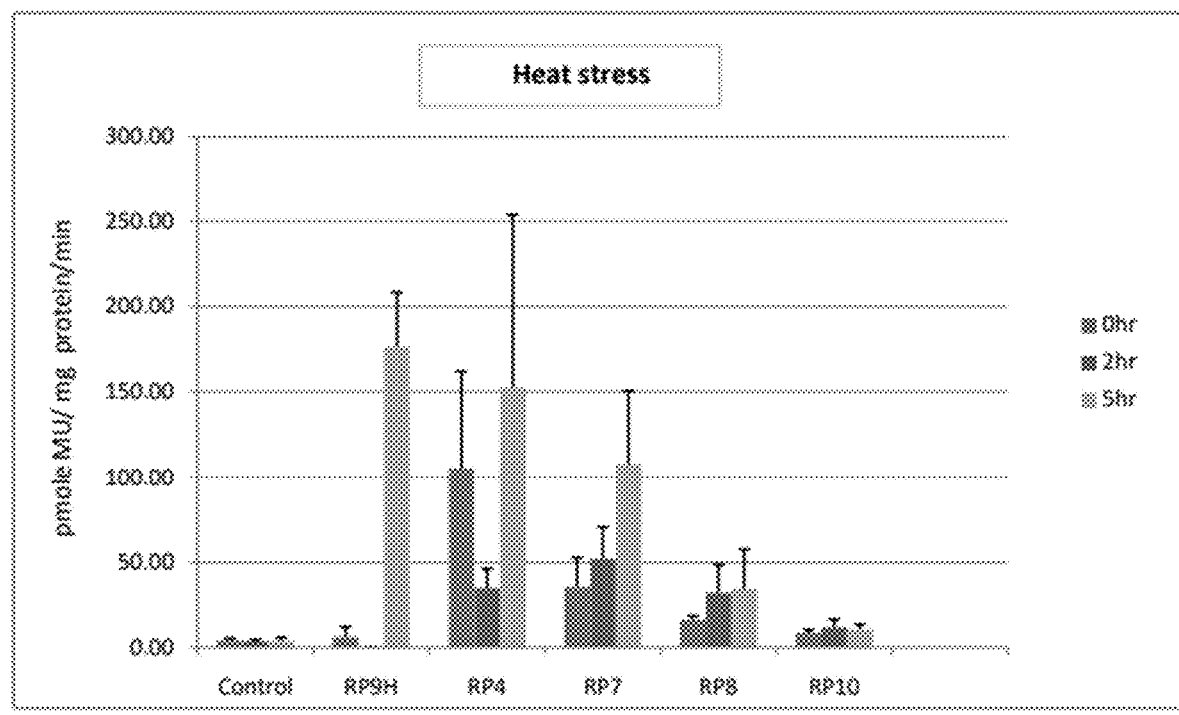
FIG. 10 is a graph of Fluorometric analysis of Gus expression in leaf tissues of different promoter viz RP2H, RP9H, RP4, RP7, RP8, RP10, RP11 after heat stress assay along with control.
Figure 11:
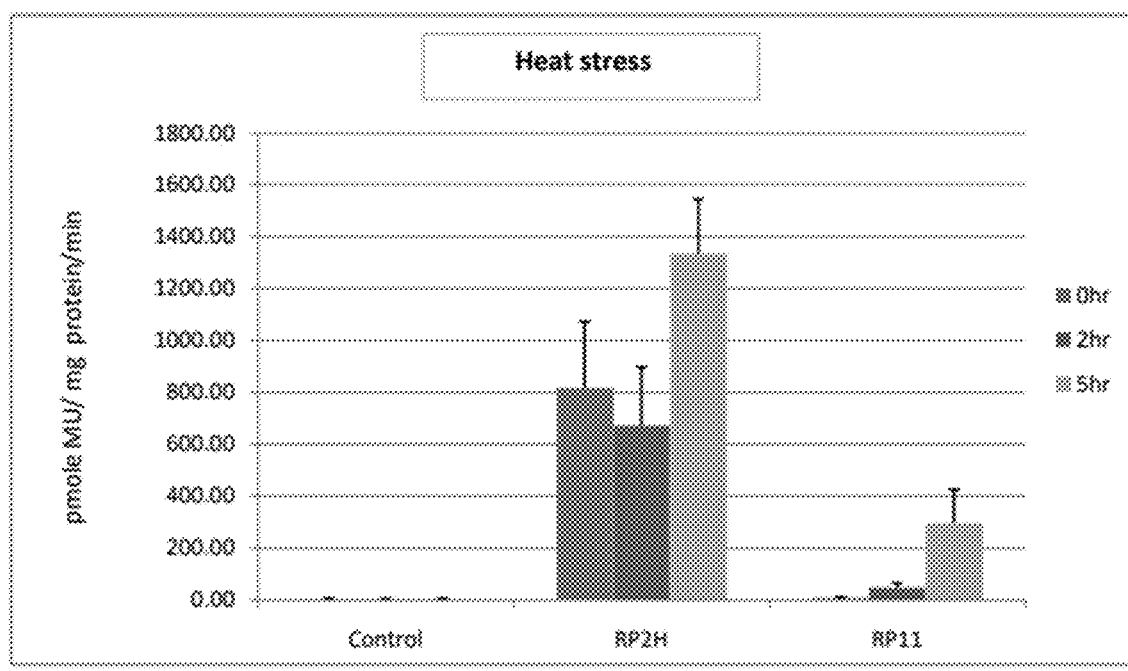
FIG. 11 is a graph of Fluorometric analysis of Gus expression in leaf tissues of different promoter viz RP2H and RP11 after heat stress assay along with control.
Figure 12:
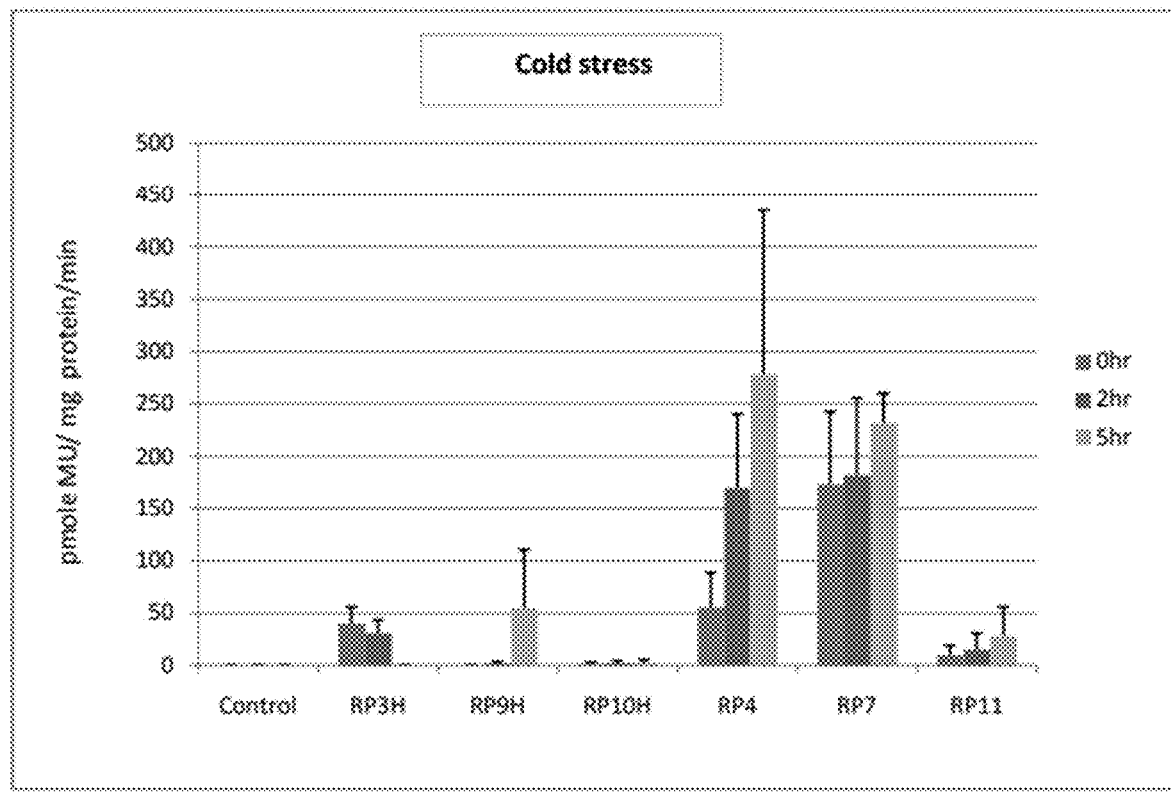
FIG. 12 is a graph of Fluorometric analysis of Gus expression in leaf tissues of different promoter viz RP3H, RP9H, RP10H, RP4, RP7, RP11 after cold stress assay along with control.
Figure 13:
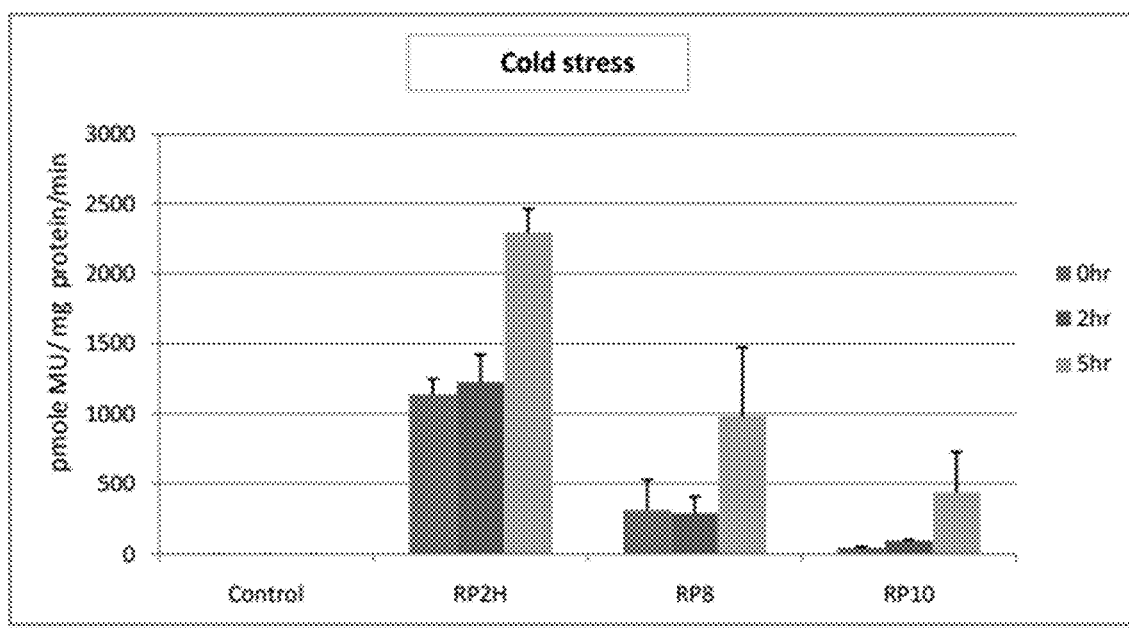
FIG. 13 is a graph of Fluorometric analysis of Gus expression in leaf tissues of different promoter viz RP2H, RP8, RP10 after cold stress assay along with control.
Figure 14:
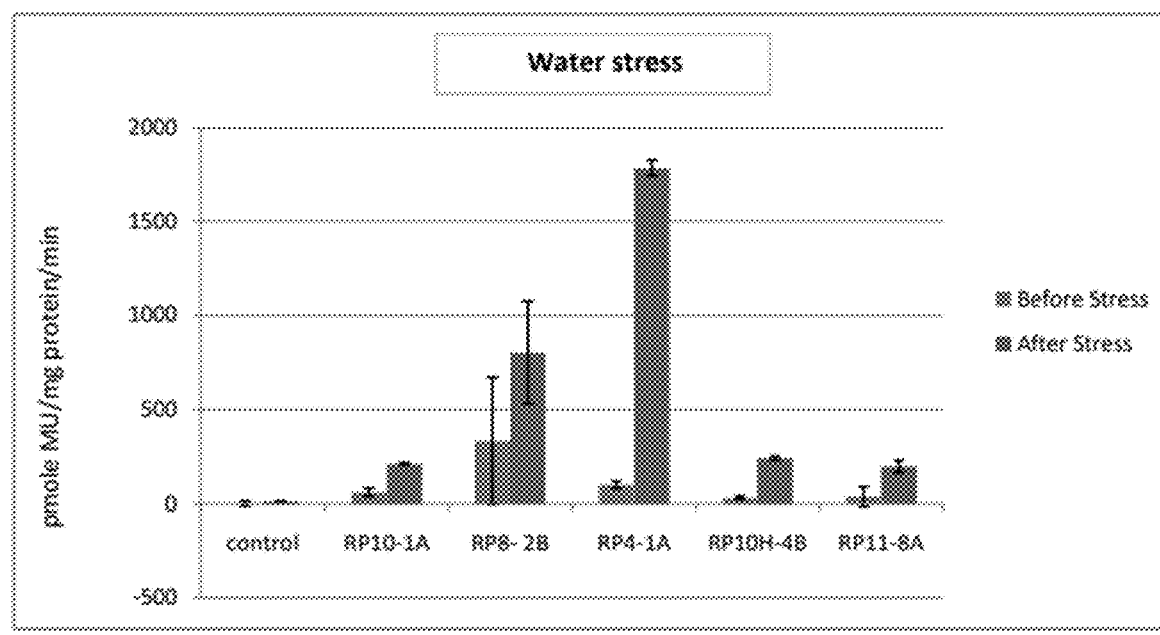
FIG. 14 is a graph of Fluorometric analysis of Gus expression in leaf tissues of different promoters viz RP10, RP8, RP4, RP10H and RP11 along with control plants when exposed to water stress condition.
Figure 15:
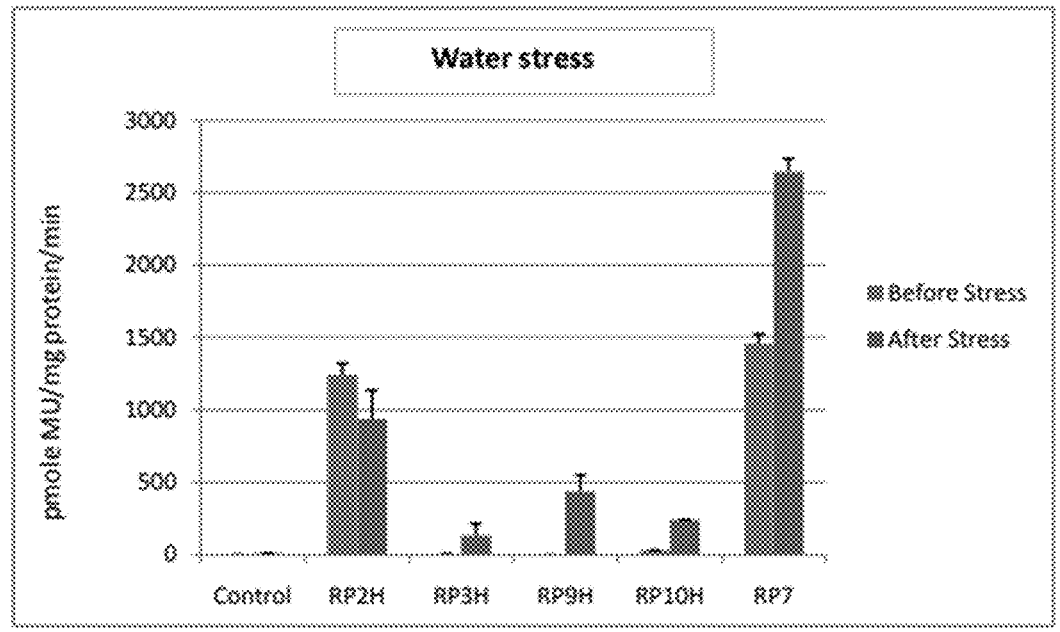
FIG. 15 is a graph of Fluorometric analysis of Gus expression in leaf tissues of different promoters viz RP2H and RP7 along with control plants after water stress assay.

Gus expression analysis of individual promoters was quantified by flurometric assay before and after water, salt, heat and cold stresses. FIGS. 8 and 9 depicts the values (i.e. pmole MU/mg protein/min) of the Gus quantification after exposing the plants OF promoter RP2H, RP3H, RP8H, RP9H, RP10H, RP4, RP7, RP8, RP10 and RP11 to 2 hours and 5 hours of salt stress. RP3H, RP9H, RP10H, RP4, RP8, and RP11 showed significant increase in the Gus expression pattern after exposing it to salt stress, whereas no significant increase in the Gus expression pattern was observed in RP2H, RP8H, RP7 and RP10 (represented by the values of table 4 and 5).

Table 6 and 7 represents significant increase in the Gus expression pattern of RP9H, RP4, RP7, RP8, RP2H and RP11 after heat stress. RP 10 showed no significant increase.

Table 8 and 9 represents the Gus expression pattern of RP2H, RP3H, RP8H, RP9H, RP10H, RP4, RP7, RP8, RP10 and RP11 to 2 hours and 5 hours of cold stress.

Table 10 represents the significant increase in the Gus expression pattern of RP10, RP8, RP4, RP10H, RP11 after water stress.

Table 11 represents the significant increase in the Gus expression pattern of RP2H, RP3H, RP9H, RP10H, RP7 after water stress.

From these tables it was concluded that RP2H behaved like a constitutive promoter which also showed inducibility to temperature variations i.e. heat and cold stress. RP9H was a stress inducible promoter which increased the expression level of a gene under salt, water, heat and cold stress condition. RP10H was water and salt stress inducible promoter. RP4 was a stress inducible promoter which increased the expression level of a gene under salt, water, heat and cold stress condition. RP7 was water, heat and cold stress inducible promoter. RP8 was water stress inducible promoter showing significant inducibility to heat and cold stress as well. RP10 is water and cold stress inducible promoter. RP11 was a stress inducible promoter which increased the expression level of a gene under various stress condition. RP3H was a water and salt stress inducible promoter. RP8H did not significantly drive Gus expression under salt, water, heat and cold stress condition.

The invention claimed is:

1. A genetic construct comprising an inducible promotor having the nucleotide sequence set forth in SEQ ID NO:7 and a heterologous polynucleotide sequence encoding a protein operably linked to said inducible promoter.

2. The genetic construct of claim 1, wherein the heterologous polynucleotide sequence encodes a beta-glucuronidase (GUS).

3. A vector comprising the genetic construct of claim 2.

4. A plant cell comprising the genetic construct of claim 2.

5. A plant cell comprising the genetic construct of claim 2 stably incorporated into its genome.

6. A transgenic plant comprising the genetic construct of claim 1 stably incorporated into its genome.

7. The transgenic plant of claim 6, wherein the transgenic plant is a monocot plant or a dicot plant.

8. The transgenic plant of claim 7, wherein the monocot plant is a rice plant.

9. Transgenic seed produced by the transgenic plant of claim 6 and comprising the genetic construct.

10. A method for regulating gene expression in a plant, the method comprising:
   a) subjecting a transgenic plant comprising the genetic construct of claim 1 to a water, cold, or salt stress condition; and
   b) investigating the expression of said protein in the plant.

11. The method of claim 10, wherein subjecting the plant to water stress is by withholding water to the plant for 1-14 days.

12. The method of claim 10, wherein subjecting the plant to salt stress is by irrigating the plant with a solution containing 100-200 mM NaCl for 2 to 12 hours.

13. The method of claim 10, wherein subjecting the plant to cold stress is by keeping the plant at a temperature of 4-8° C. for 2-8 hours.

* * * * *